US009592075B2

(12) United States Patent
Simpson et al.

(10) Patent No.: US 9,592,075 B2
(45) Date of Patent: Mar. 14, 2017

(54) ATHERECTOMY CATHETERS DEVICES HAVING MULTI-CHANNEL BUSHINGS

(71) Applicant: Avinger, Inc., Redwood City, CA (US)

(72) Inventors: John B. Simpson, Woodside, CA (US); Himanshu N. Patel, San Jose, CA (US); Anthony J. Fernandez, San Mateo, CA (US); Richard R. Newhauser, Redwood City, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 15/072,272

(22) Filed: Mar. 16, 2016

(65) Prior Publication Data

US 2016/0192962 A1    Jul. 7, 2016

Related U.S. Application Data

(63) Continuation-in-part of application No. PCT/US2015/014613, filed on Feb. 5, 2015.
(Continued)

(51) Int. Cl.
*A61B 17/22*    (2006.01)
*A61D 1/02*    (2006.01)
(Continued)

(52) U.S. Cl.
CPC .... *A61B 17/320783* (2013.01); *A61B 5/0066* (2013.01); *A61B 5/0084* (2013.01); *A61B 17/320758* (2013.01); *A61M 25/0043* (2013.01); *A61M 25/0068* (2013.01); *A61M 25/0074* (2013.01); *A61M 25/0082* (2013.01);
(Continued)

(58) Field of Classification Search
CPC .... A61B 17/320758; A61B 17/320783; A61B 2017/320791; A61B 5/0066; A61B 17/32002; A61B 2017/2927; A61B 2017/320032; A61B 2090/3614;
(Continued)

(56) References Cited

U.S. PATENT DOCUMENTS 4,178,935 A    12/1979    Gekhaman et al.
4,527,553 A    7/1985    Upsher
(Continued)

FOREIGN PATENT DOCUMENTS

CN    1875242 A    12/2006
CN    1947652 A    4/2007
(Continued)

OTHER PUBLICATIONS

Aziz et al.; Chronic total occlusions—a stiff challege requiring a major breakthrough: is there light at the end of the tunnel?; Heart; vol. 91; suppl. III; pp. 42-48; Jun. 2005.
(Continued)

*Primary Examiner* — Katherine M Shi
(74) *Attorney, Agent, or Firm* — Shay Glenn LLP

(57) ABSTRACT

Atherectomy catheters and methods of using them are described herein. In particular, described herein are optical coherence tomography (OCT) catheters that may include a distal tip that can be deflected away from the long axis of the device using a multi-channel bushing. The bushing may include at a hinge point that is offset (e.g., located on a side of the elongate body near the distal end of the elongate body) and a rotatable cutter near an imaging assembly that can be driven against the wall with a high mechanical advantage.

20 Claims, 23 Drawing Sheets

Related U.S. Application Data

(60) Provisional application No. 61/936,837, filed on Feb. 6, 2014.

(51) Int. Cl.
*A61B 17/3207* (2006.01)
*A61B 5/00* (2006.01)
*A61M 25/00* (2006.01)

(52) U.S. Cl.
CPC ............. *A61B 2017/320791* (2013.01); *A61B 2090/3735* (2016.02)

(58) Field of Classification Search
CPC ......... A61B 2090/3735; A61B 5/0084; A61M 2025/0096; A61M 25/0082
USPC .............................................. 606/159; 604/22
See application file for complete search history.

(56) References Cited

U.S. PATENT DOCUMENTS

| | | |
|---|---|---|
| 4,552,554 A | 11/1985 | Gould et al. |
| 4,621,353 A | 11/1986 | Hazel et al. |
| 4,639,091 A | 1/1987 | Huignard et al. |
| 4,654,024 A | 3/1987 | Crittenden et al. |
| 4,686,982 A | 8/1987 | Nash |
| 4,771,774 A | 9/1988 | Simpson et al. |
| 4,841,977 A | 6/1989 | Griffith et al. |
| 4,926,858 A | 5/1990 | Gifford, III et al. |
| 5,000,185 A | 3/1991 | Yock |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,383,460 A | 1/1995 | Jang et al. |
| 5,383,467 A | 1/1995 | Auer et al. |
| 5,429,136 A | 7/1995 | Milo et al. |
| 5,431,673 A | 7/1995 | Summers et al. |
| 5,459,570 A | 10/1995 | Swanson et al. |
| 5,465,147 A | 11/1995 | Swanson |
| 5,507,795 A | 4/1996 | Chiang et al. |
| 5,556,405 A | 9/1996 | Lary |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,779 B1 | 9/2002 | Taylor |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,615,071 B1 | 9/2003 | Casscells, III et al. |
| 6,638,233 B2 | 10/2003 | Corvi et al. |
| 6,645,217 B1 | 11/2003 | MacKinnon et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |

(56) References Cited

U.S. PATENT DOCUMENTS

| | | |
|---|---|---|
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,706,863 B2 | 4/2010 | Imanishi et al. |
| 7,728,985 B2 | 6/2010 | Feldchtein et al. |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,644,913 B2 | 2/2014 | Simpson et al. |
| 8,696,695 B2 | 4/2014 | Patel et al. |
| 9,125,562 B2 | 9/2015 | Spencer et al. |
| 2001/0020126 A1 | 9/2001 | Swanson et al. |
| 2002/0019644 A1 | 2/2002 | Hastings et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1 | 10/2002 | Wood |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0082850 A1 | 4/2004 | Bonner et al. |
| 2004/0092915 A1 | 5/2004 | Levatter |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri et al. |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |

(56) References Cited

U.S. PATENT DOCUMENTS

| | | |
|---|---|---|
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0125253 A1 | 5/2010 | Olson |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0023617 A1 | 2/2011 | Yu et al. |
| 2011/0040238 A1 | 2/2011 | Wulfman et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0270187 A1 | 11/2011 | Nelson |
| 2011/0301625 A1 | 12/2011 | Mauch et al. |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0289971 A1 | 11/2012 | Segermark et al. |
| 2013/0035692 A1 | 2/2013 | Sorensen et al. |
| 2013/0096589 A1 | 4/2013 | Spencer et al. |
| 2013/0123615 A1 | 5/2013 | Spencer et al. |
| 2013/0138128 A1 | 5/2013 | Patel et al. |
| 2013/0289392 A1 | 10/2013 | Patel et al. |
| 2013/0296695 A1 | 11/2013 | Spencer et al. |
| 2013/0317519 A1 | 11/2013 | Romo et al. |
| 2014/0005534 A1 | 1/2014 | He et al. |
| 2014/0213893 A1 | 7/2014 | Simpson et al. |
| 2015/0099984 A1 | 4/2015 | Kankaria |
| 2015/0126856 A1 | 5/2015 | Tachibana et al. |
| 2015/0141816 A1 | 5/2015 | Gupta et al. |
| 2015/0164530 A1 | 6/2015 | Carver et al. |
| 2015/0208922 A1 | 7/2015 | Simpson et al. |
| 2015/0272615 A1 | 10/2015 | Newhauser et al. |
| 2015/0320975 A1 | 11/2015 | Simpson et al. |
| 2016/0008025 A1 | 1/2016 | Gupta et al. |
| 2016/0029902 A1 | 2/2016 | Smith et al. |
| 2016/0038030 A1 | 2/2016 | Smith et al. |
| 2016/0262791 A1 | 9/2016 | Patel et al. |
| 2016/0262839 A1 | 9/2016 | Spencer et al. |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-83057 A | 4/2007 |
| JP | 2007-225349 A | 9/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-78150 A | 4/2009 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO 01/76680 A1 | 10/2001 |
| WO | WO 2006/133030 A2 | 12/2006 |
| WO | WO 2008/029506 A1 | 3/2008 |
| WO | WO 2008/042987 A2 | 4/2008 |
| WO | WO 2008/065600 A2 | 6/2008 |
| WO | WO 2008/086613 A1 | 7/2008 |
| WO | WO 2008/087613 A2 | 7/2008 |
| WO | WO 2009/005779 A1 | 1/2009 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A1 | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2010/039464 A1 | 4/2010 |
| WO | WO2010/056771 A1 | 5/2010 |
| WO | WO 2012/061935 A1 | 5/2012 |
| WO | WO2012/166332 A1 | 12/2012 |

(56) References Cited

FOREIGN PATENT DOCUMENTS

| WO | WO 2015/120146 A1 | 8/2015 |
|---|---|---|
| WO | WO 2016/007652 A1 | 1/2016 |

OTHER PUBLICATIONS

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Linares et al.; Arbitrary single-mode coupling by tapered and nontapered grin fiber lenses; Applied Optics; vol. 29; No. 28; pp. 4003-4007; Oct. 1, 1990.

Sharma et al.; Optical coherence tomography based on an all-fiber autocorrelator using probe-end reflection as reference; CWJ13; San Francisco, California; CLEO May 16, 2004; 4 pages.

Suparno et al.; Light scattering with single-mode fiber collimators; Applied Optics; vol. 33; No. 30; pp. 7200-7205; Oct. 20, 1994.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Simpson et al.; U.S. Appl. No. 14/899,877 entitled "Occlusion sheath for imaging catheter," filed Dec. 18, 2015.

Simpson et al.; U.S. Appl. No. 14/899,893 entitled "Identification of elastic lamina to guide interventional therapy," filed Dec. 18, 2015.

Patel et al.; U.S. Appl. No. 15/076,568 entitled "Atherectomy catheters and occlusion crossing devices," filed Mar. 21, 2016.

Tachibana et al.; U.S. Appl. No. 15/162,391 entitled "Atherectomy catheter drive assemblies," filed May 23, 2016.

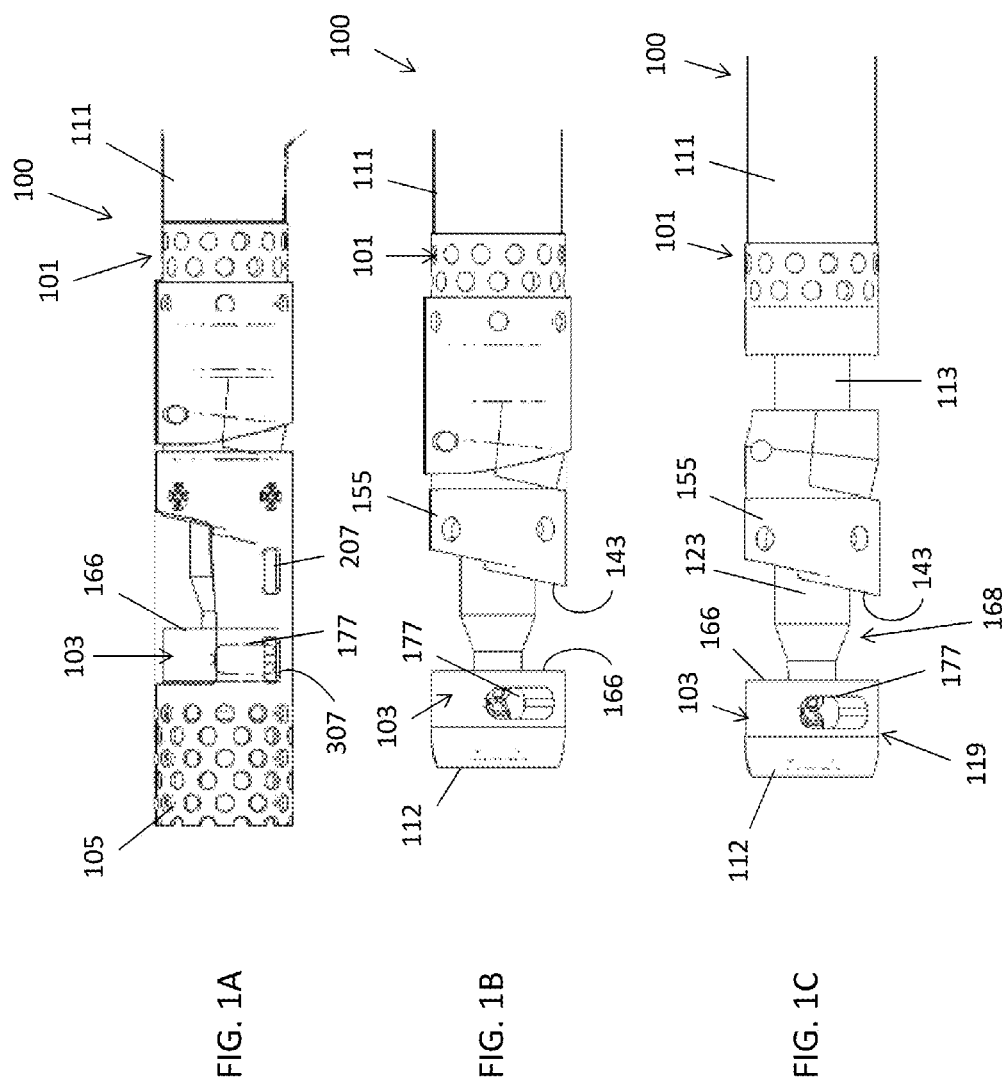

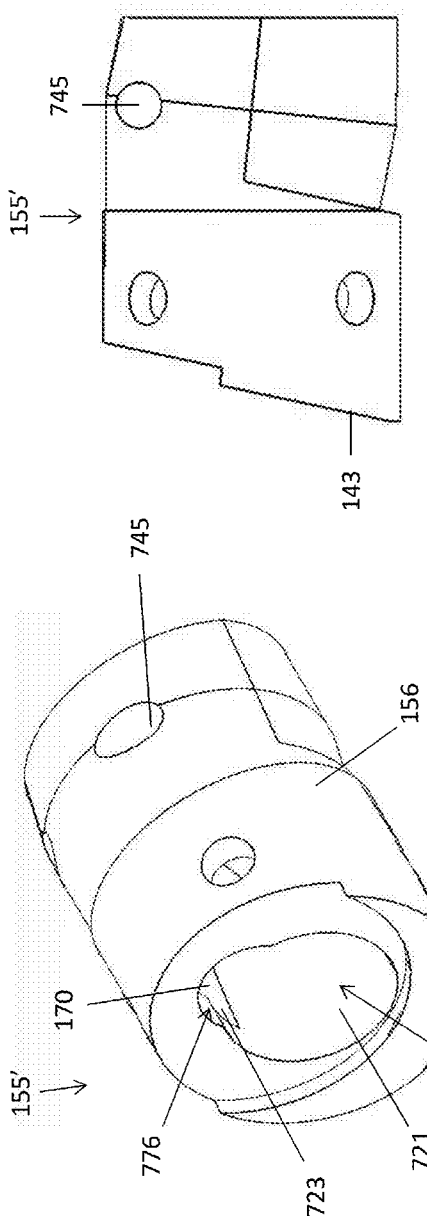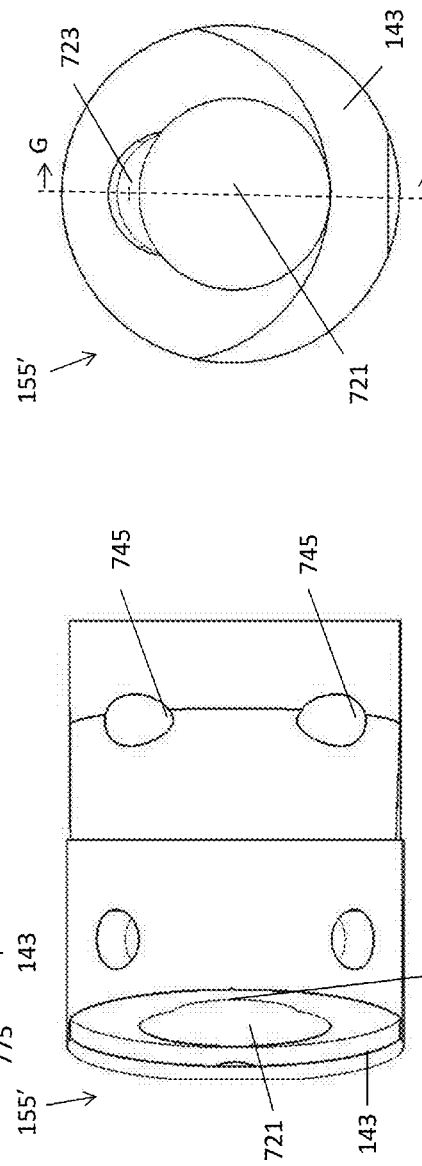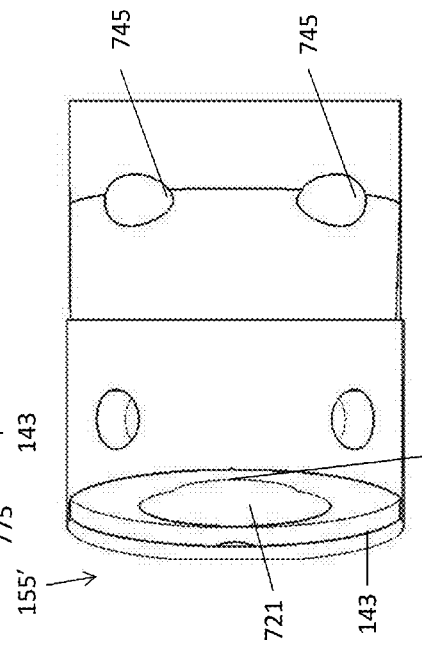

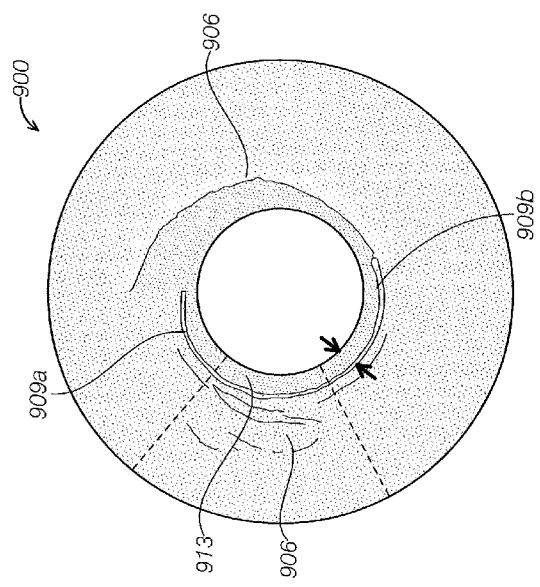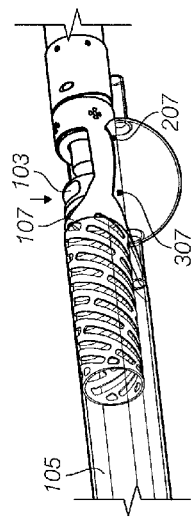
FIG. 9A
FIG. 9B
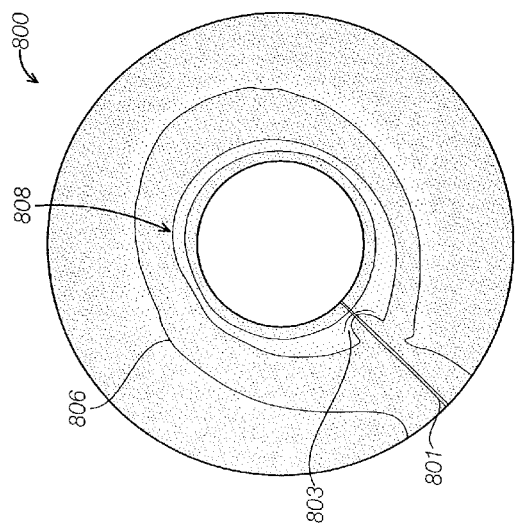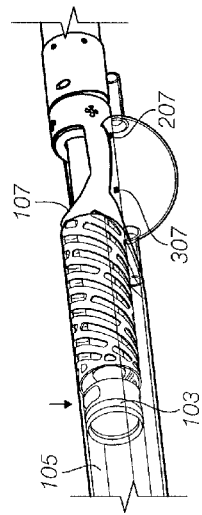
FIG. 8A
FIG. 8B

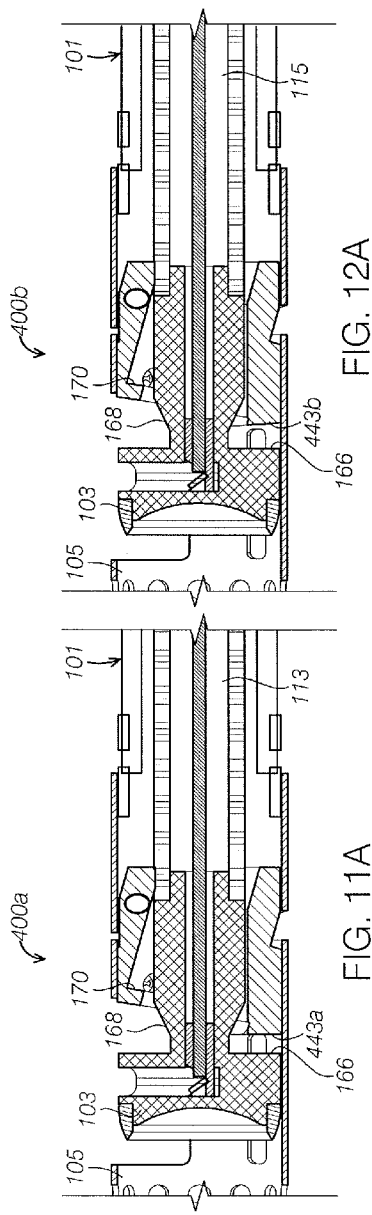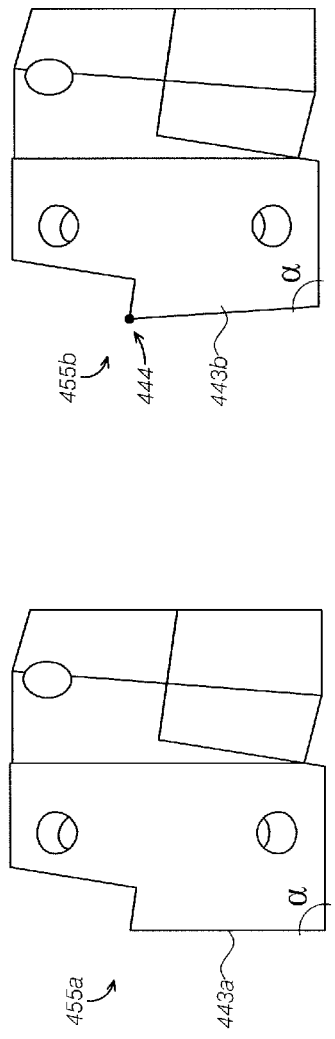
FIG. 11A  FIG. 12A  FIG. 11B  FIG. 12B

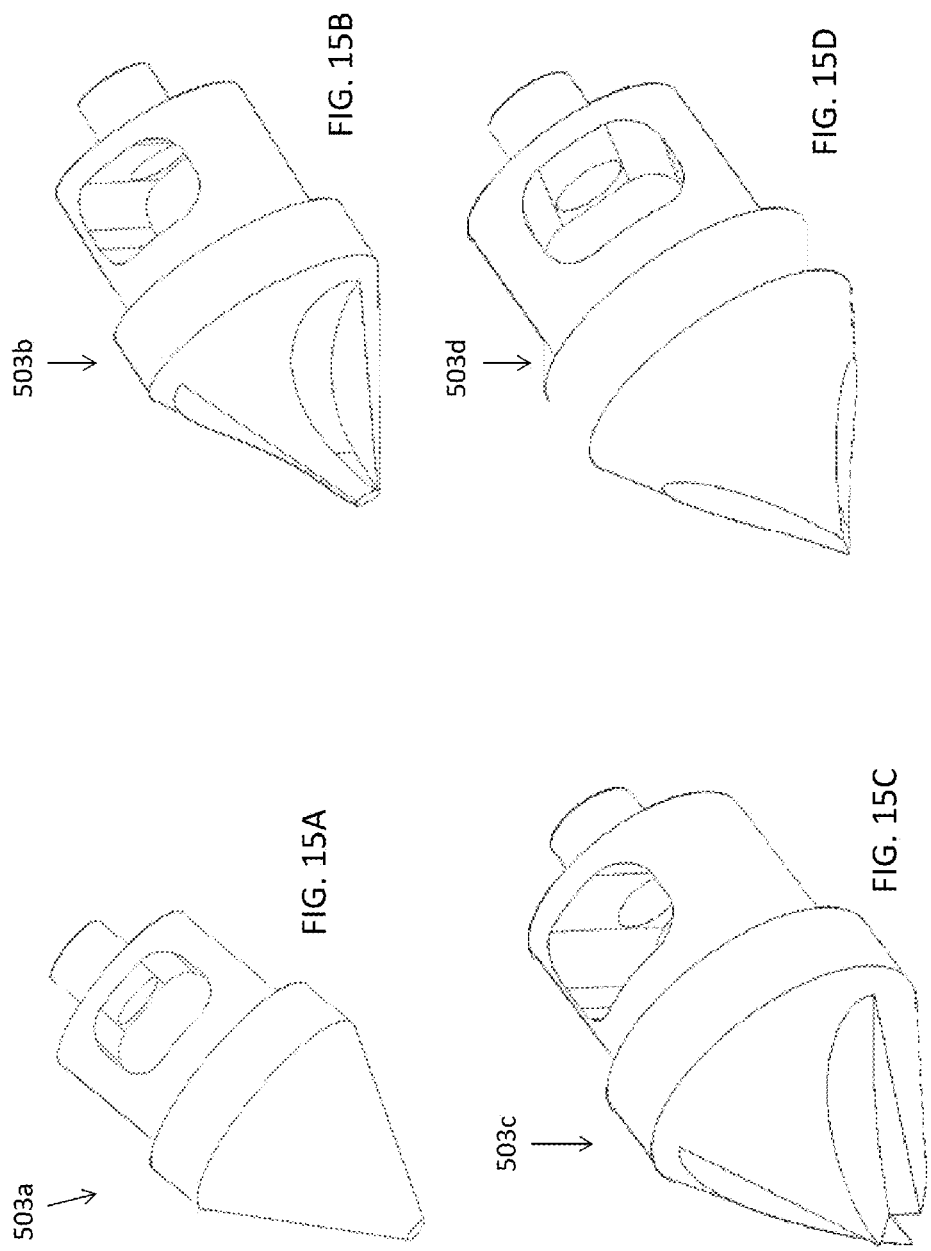

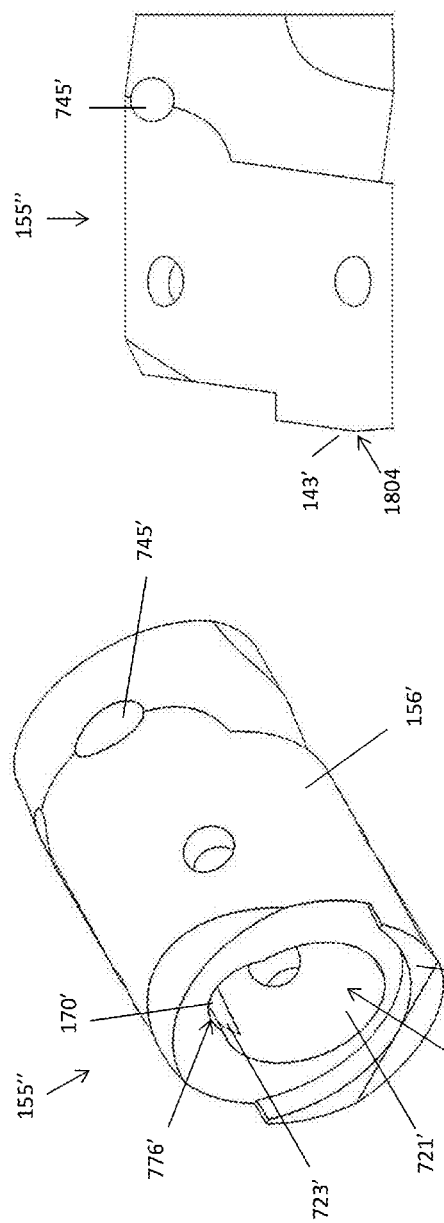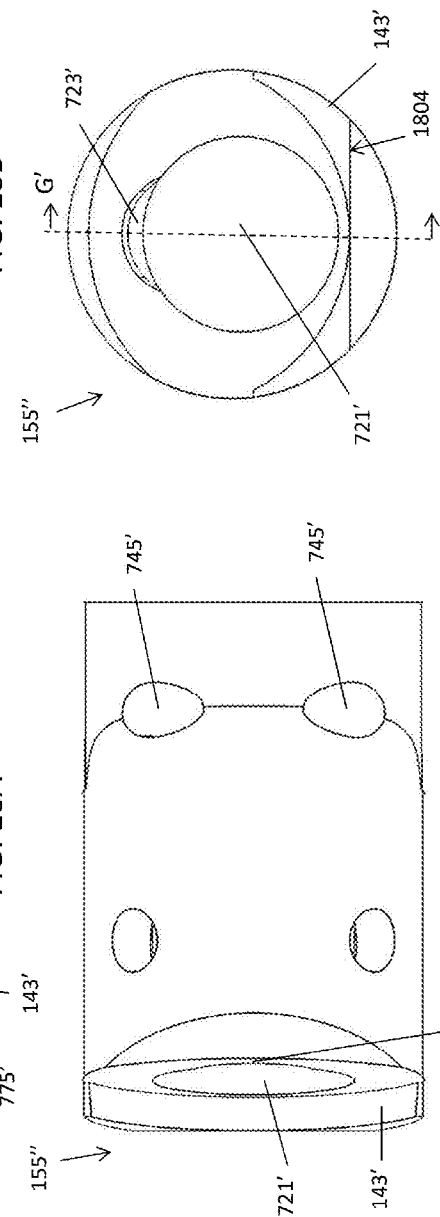

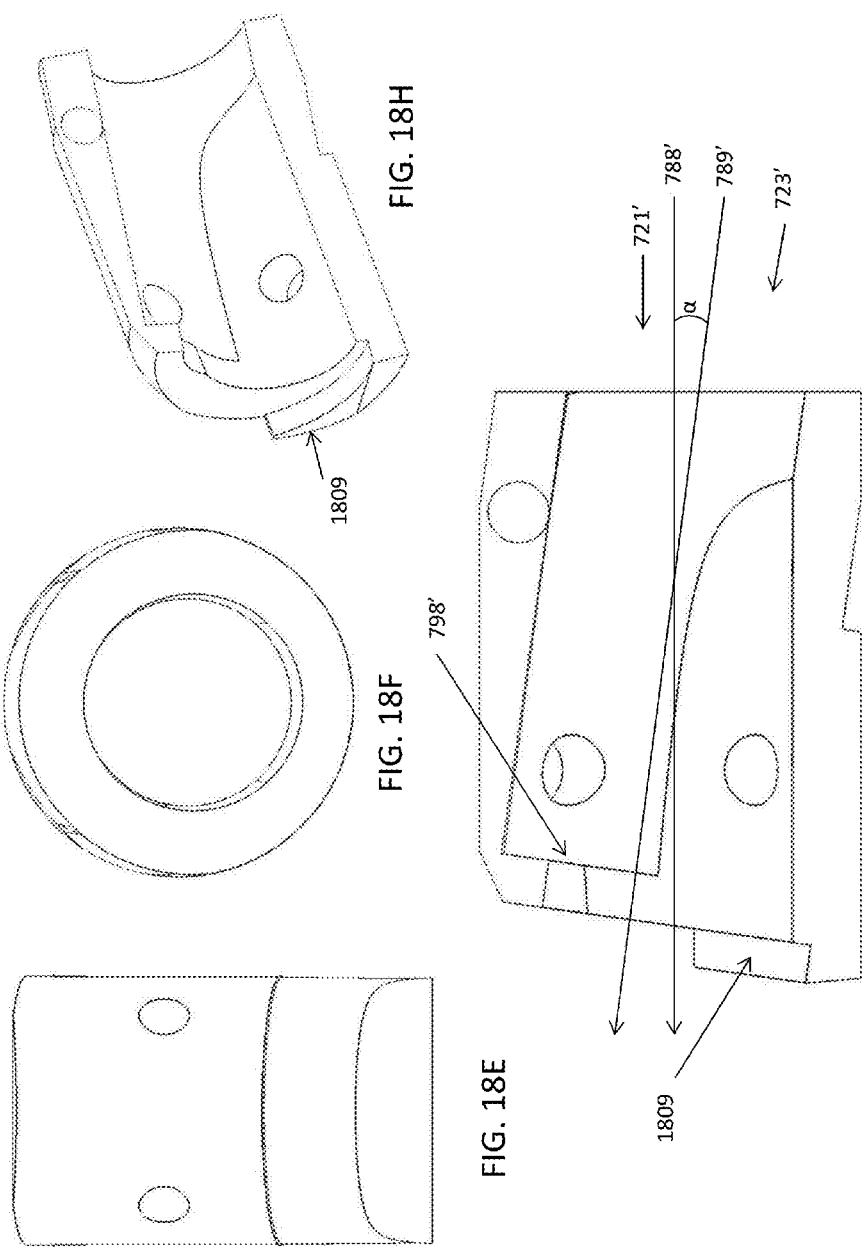

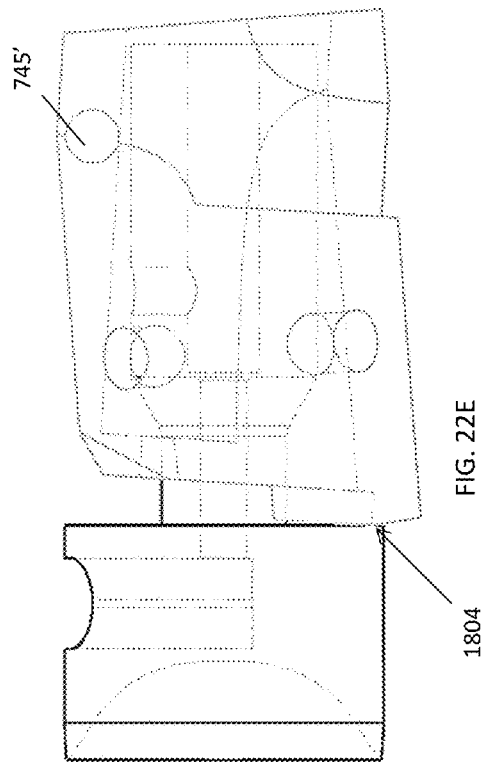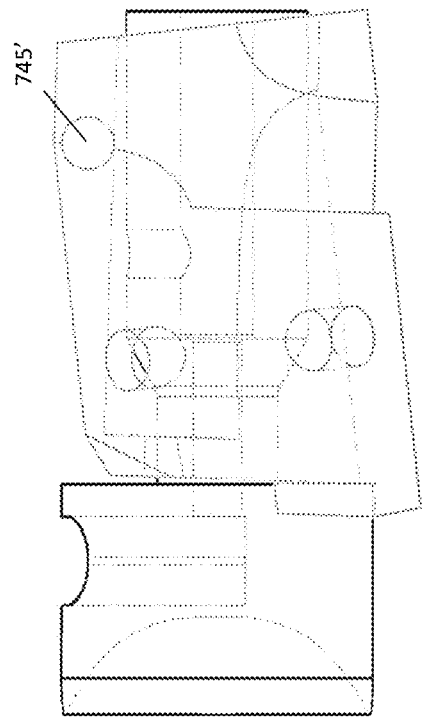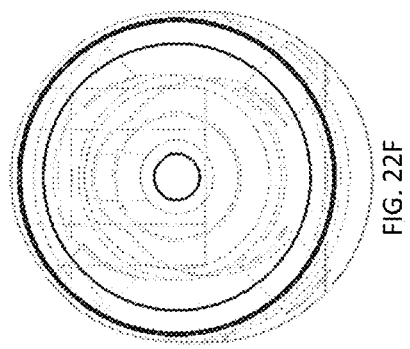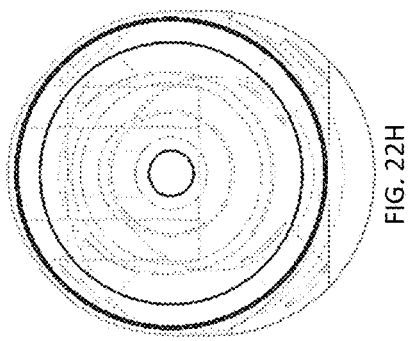

ATHERECTOMY CATHETERS DEVICES HAVING MULTI-CHANNEL BUSHINGS

CROSS REFERENCE TO RELATED APPLICATIONS

This application claims priority as a continuation-in-part of International Patent Application No. PCT/US2015/014613, titled "ATHERECTOMY CATHETERS AND OCCLUSION CROSSING DEVICES", filed Feb. 5, 2015, which claimed priority to U.S. Provisional Patent Application No. 61/936,837, titled "ATHERECTOMY CATHETERS AND OCCLUSION CROSSING DEVICES," filed Feb. 6, 2014, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are atherectomy catheters and methods of using them. In particular, described herein are atherectomy catheters that include a bushing configured to be hinged off-axis and include two overlapping channels through which a central cutter and/or rotating driver may move. The multi-channel bushing allows reliable and low-force displacement of a distal tip to expose a cutter.

BACKGROUND

Peripheral artery disease (PAD) and coronary artery disease (CAD) affect millions of people in the United States alone. PAD and CAD are silent, dangerous diseases that can have catastrophic consequences when left untreated. CAD is the leading cause of death in the United States while PAD is the leading cause of amputation in patients over 50 and is responsible for approximately 160,000 amputations in the United States each year.

Coronary artery disease (CAD) and Peripheral artery disease (PAD) are both caused by the progressive narrowing of the blood vessels most often caused by atherosclerosis, the collection of plaque or a fatty substance along the inner lining of the artery wall. Over time, this substance hardens and thickens, which can cause an occlusion in the artery, completely or partially restricting flow through the artery. Blood circulation to the arms, legs, stomach and kidneys brain and heart may be reduced, increasing the risk for stroke and heart disease.

Interventional treatments for CAD and PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Often, occlusion-crossing devices can be used to ease the passage of such devices through a blockage.

Minimally invasive techniques can be enhanced through the use of on-board imaging, such as optical coherence tomography ("OCT") imaging. Images obtained from an atherectomy device, however, can be inaccurate due to the placement of the imaging sensor at a location that is far from the cutter. As a result, it can be difficult to visualize the tissue being cut. Moreover, minimally-invasive techniques can be inefficient, as often many devices are required to perform a single procedure.

Although atherectomy devices having a distal cutting edge that can be covered and exposed by moving a distal tip have been described, the forces necessary to displace the distal tip reliably and repeatedly have proven undesirably large and difficult to operate reliably. Described herein are atherectomy catheter devices, occlusion-crossing devices, and the corresponding systems and methods that may address some of these concerns.

SUMMARY OF THE DISCLOSURE

In general, described herein are atherectomy catheters and methods of using them.

In particular, described herein are optical coherence tomography (OCT) catheters that may include one or more of the features illustrated, discussed and described herein in any combination.

For example, described herein are atherectomy catheter devices having a multi-channeled bushings. Any of these atherectomy catheter devices may include: an elongate body; a tip extending from a distal end of the elongate body; a drive shaft extending within the elongate body; a bushing comprising a bushing body, a hinge point on a side of the bushing body, a first channel extending proximally to distally through the bushing body, a second channel extending proximally to distally through the bushing body, overlapping with the first channel and having a diameter of the second channel that is less than a diameter of the first channel, and wherein the second channel is angled between 1° and 45° relative to the first channel, a first opening at a distal end of the bushing body into the first channel, and a second opening at the distal end of the bushing body into the second channel, wherein the first and second openings overlap; and a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing and drives the tip about the hinge point to axially align the tip with the elongate body and at least partially cover the cutting edge, while proximal movement of the drive shaft extends the neck region of the cutter within the second channel of the bushing and drives the tip about the hinge point to angle the tip relative to the elongate body and at least partially expose the cutting edge.

Any of these bushings may also or alternatively comprise an inner flange positioned distal to the hinge, wherein distal movement of the drive shaft extends the cylindrical body of the cutter within the first channel of the bushing and drives the neck region against the inner flange portion to drive the tip about the hinge point to axially align the tip with the elongate body. The inner flange may include a face that is angled relative to the long axis of the elongate body. For example the inner flange may be angled at an angle of between about 2° (degrees) and about 90° (e.g., between about 5° and about 45°, between about 5° and 30°, etc.).

Any of these devices may include outer flange at the distal end of the bushing, wherein proximal movement of the drive shaft extends the neck region of the cutter within the second channel of the bushing and drives the distal cutting head against the outer flange portion to drive the tip about the hinge point to angle the tip relative to the elongate body. The outer flange may include a face that is angled relative to the long axis of the elongate body. For example, the outer flange may be angled at an angle of between about 2° and about 90° (e.g., between about 5° and about 45°, between about 5° and about 30°, etc.).

In any of these devices, the second channel may be angled relative to the first channel between about 2° and 45°, between about 2° and 30°, between about 2° and 20°, etc.

In any of these devices, the hinge point may be one of a pair of hinge points that are on either side of the bushing body and offset from a midline along a distal-to-proximal axis of the bushing body. The hinge point or hinge points may be part of a hinge channel formed through a top peripheral region of the bushing body, further wherein the hinge channel extends in a direction that is transverse to the first channel. The hinge point is generally located toward the proximal end of the bushing and may be positioned longitudinally along the proximal-to-distal axis of the bushing within the proximal 40%, 30%, 20%, 10% of the proximal end of the bushing.

Any of the apparatuses (e.g., catheter devices, atherectomy devices, etc.) described herein may be configured to provide imaging, including optical coherence tomography imaging. For example, and of these apparatuses may include an optical fiber extending though the drive shaft and coupled to a reflector in the cutter to form an optical coherence tomography (OCT) imaging sensor.

In general the cutter (which may also be referred to as a cutting assembly and/or cutting an imaging assembly) may be configured to rotate within the bushing. For example, the elongate cylindrical body of the cutter may be configured to rotate within the bushing.

The tip of any of these devices may be a hollow tip and may be configured for packing cut tissue (e.g., in conjunction with the cutter). For example, the cutter may be configured to extend beyond the bushing and into the tip to pack tissue into the tip.

An atherectomy catheter device having a multi-channeled bushing may include: an elongate body; a tip extending from a distal end of the elongate body; a drive shaft extending within the elongate body; a bushing comprising a bushing body, a pair of hinge points on either side of the bushing body that are offset from a midline along a distal-to-proximal axis of the bushing body, an inner flange positioned distal to the hinge points, a first channel extending proximally to distally through the bushing body, a second channel extending proximally to distally through the bushing body and having a diameter along a length of the second channel that is less than a diameter along a length of the first channel, and wherein the first and the second channels overlap, and wherein the second channel is angled between 1° and 45° relative to the first channel, a first opening at a distal end of the bushing body into the first channel, and a second opening at a distal end of the bushing body into the second channel, wherein the first and second openings overlap, and an outer flange portion distal to the inner flange portion; and a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing, drives the neck region against the inner flange portion and drives the tip about the hinge points to axially align the tip with the elongate body at least partially covering the cutting edge, while proximal movement of the drive shaft extends the neck region of the cutter within the second channel of the bushing, drives the distal cutting head against the outer flange portion, and drives the tip about the hinge points to angle the tip relative to the elongate body and at least partially expose the cutting edge.

An atherectomy catheter device having a multi-channeled bushing may include: an elongate body; a hollow distal tip extending from a distal end of the elongate body; a drive shaft extending within the elongate body; a bushing comprising a bushing body, a pair of hinge points on either side of the bushing body that are offset from a midline along a distal-to-proximal axis of the bushing body, an inner flange positioned distal to the hinge points a first channel extending proximally to distally through the bushing body, a second channel extending proximally to distally through the bushing body and having a diameter along a length of the second channel that is less than a diameter along a length of the first channel, and wherein the first and the second channels overlap, and wherein the second channel is angled between 1° and 45° relative to the first channel, a first opening at a distal end of the bushing body into the first channel, and a second opening at a distal end of the bushing body into the second channel, wherein the first and second openings overlap, and an outer flange portion distal to the inner flange portion; a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing and drives the hollow distal tip about the hinge points to axially align the hollow distal tip with the elongate body at least partially covering the cutting edge, while proximal movement of the drive shaft extends the neck region of the cutter within the second channel of the bushing and drives the hollow distal tip about the hinge points to angle the hollow distal tip relative to the elongate body and at least partially expose the cutting edge.

Also described herein are catheters having a distal tip that can be deflected away from the long axis of the device at a hinge point that is offset (e.g., located on a side of the elongate body near the distal end of the elongate body). The distal tip may include a bushing that is hinged to the body and interacts with a necked region of a rotatable imaging and/or cutting assembly to displace and/or restore the distal tip. The catheter may be configured so that the distal tip is displaced by a first mechanism (e.g., a pneumatic mechanism, a pull tendon, etc.) and is restored by a second mechanism, such as the lateral motion of the imaging/cutting assembly. The device described herein may be configured so that the status of the distal tip (e.g., displacement, filling) may be detected or determined with the OCT imaging that also images the region around the perimeter of the imaging/cutting assembly of the catheter (e.g., the vessel). For example, the device may be configured so that the distal tip displacement is visible in the OCT images to provide direct feedback on the cutting status (ready to cut/not ready to cut) of the atherectomy device.

Also described herein are catheters configured to provide a mechanical advantage when driving a lateral cutting edge against the wall of a vessel that surrounds the catheter. For example, the atherectomy device may include a pair of balloons at the distal end of the device that are separated slightly apart from each other; the first balloon that is located near the cutter pushes the cutter towards the wall of the vessel while the proximally located balloon pushes in an opposite direction, pivoting just the end region of the catheter against the wall of the vessel from the pivot point established by the second (e.g., fulcrum) balloon. As another example, the catheter can include a single crescent-shaped balloon configured to both urge the cutter against the wall and occlude the vessel.

Also described herein are catheters including high-powered flushing 'jets' that can be used to pack material (cut material) into the hollow nosecone, as well as to clear the imaging region. These jet flushing ports may also be configured to create a venturi effect that can be used to suck material into the nosecone and/or away from the imaging/cutting head and/or the distal end region of the elongate body.

Also described herein are techniques and structures for managing the optical fiber at the proximal end (e.g., the handle) of the catheter. In devices in which the optical fiber and drive shaft rotate and may move laterally (proximally/distally), an optical fiber management chamber at the proximal end of the device before the coupling region for coupling the optical fiber to the imaging system. The optical fiber management chamber may be cylindrical. The optical fiber management chamber typically includes a hollow space in which the fiber, as it moves laterally relative to the proximal coupling region, may safely bend. The optical fiber management chamber rotates with the optical fiber, so there is no relative rotational motion between the optical fiber management chamber and the optical fiber.

Also described herein are general occlusion crossing devices having cutting tips that may be swapped out.

In general, in one embodiment, an atherectomy catheter device includes an elongate body, a hollow distal tip, a drive shaft, a bushing, and a cutting and imaging assembly. The hollow distal tip extends from a distal end of the elongate body. The drive shaft extends distally to proximally within the elongate body. The bushing is coupled to the distal tip and has a hinge point connected to one side of the elongate body and an inner flange positioned distal to the hinge point. The cutting and imaging assembly is coupled to the drive shaft and has a distal cutting edge and a neck region that passes through the bushing. Distal movement of the drive shaft within the bushing causes the inner flange to move along the neck region of the cutting and imaging assembly, rotating the hollow distal tip and bushing about the hinge point and axially aligning the hollow distal tip with the elongate body to at least partially cover the distal cutting edge.

This and other embodiments can include one or more of the following features. The bushing can have distal end face. Proximal movement of the drive shaft within the bushing can cause a proximal surface of the cutting and imaging assembly to slide along at least a portion of the distal end face to pivot the bushing and hollow tip about the hinge point and expose the distal cutting edge. The distal end face can be angled relative to a central longitudinal axis of the elongate body. The angle can be greater than 90 degrees. The angle can be less than 90 degrees. The distal end face can be perpendicular to a central longitudinal axis of the elongate body. The bushing can further include a first channel therethrough and a second channel extending at an angle relative to the first channel. The second channel can overlap with the first channel, and the neck region can sit within the first channel when the hollow distal tip is aligned with the elongate body and through the second channel when the hollow distal tip is angled relative to the elongate body. The bushing can include a hinge channel formed through a top peripheral region of the bushing. The hinge channel can extend in a direction that is transverse to the first channel.

The device can further include an optical fiber extending though the drive shaft and coupled to a reflector in the cutting and imaging assembly to form an optical coherence tomography (OCT) imaging sensor. The cutting and imaging assembly can be configured to rotate within the bushing. The cutting and imaging assembly can be configured to extend beyond the bushing and into the hollow distal tip to pack tissue into the hollow distal tip.

In general, in one embodiment, an atherectomy catheter device includes an elongate body, a hollow distal tip, a drive shaft, a bushing, and a cutting and imaging assembly. The hollow distal tip extends from a distal end of the elongate body. The drive shaft extends distally to proximally within the elongate body. The bushing is coupled to the hollow distal tip and has a hinge point connected to one side of the elongate body and a distal face that is angled at less than 90 degrees relative to a central longitudinal axis of the elongate body such that an inner distal edge is formed. The cutting and imaging assembly is coupled to the drive shaft and has a distal cutting edge and a proximal surface. Proximal movement of the drive shaft within the bushing causes the proximal surface of the cutting and imaging assembly to slide along the inner distal edge of the bushing to pivot the bushing and hollow distal tip about the hinge point to expose the distal cutting edge.

This and other embodiments can include one or more of the following features. The cutting and imaging assembly can further include a necked region configured to sit within the bushing. The bushing can further include a first channel through the bushing and a second channel extending at an angle relative to the first channel. The second channel can overlap with the first channel, and the neck region can sit within the first channel when the hollow distal tip is aligned with the elongate body and through the second channel when the hollow distal tip is angled relative to the elongate body. The bushing can include a hinge channel formed through a top peripheral region of the bushing. The hinge channel can extend in a direction that is transverse to the first elongate channel. The device can further include an optical fiber extending though the drive shaft and coupled to a reflector in the cutting and imaging assembly to form an optical coherence tomography (OCT) imaging sensor. The cutting and imaging assembly can be configured to rotate within the bushing. The cutting and imaging assembly can be configured to extend beyond the bushing and into the hollow distal tip to pack tissue into the hollow distal tip.

In general, in one embodiment, an atherectomy catheter device includes an elongate body, a hollow distal tip, a drive shaft, an optical coherence tomography fiber, and a cutting and imaging assembly. The hollow distal tip extends from a distal end of the elongate body. The drive shaft extends distally to proximally within the elongate body. The optical coherence tomography fiber runs along a central longitudinal axis of the drive shaft an entire length of the drive shaft. The cutting and imaging assembly is coupled to the drive shaft and has a distal cutting edge and a slot configured to hold a distal end of the fiber therein. The slot has a length that is equal to or greater than a radius of the cutting and imaging assembly such that the optical fiber extends from the drive shaft straight through the cutting and imaging assembly into the slot without bending.

This and other embodiments can include one or more of the following features. Proximal or distal movement of the drive shaft can cause the hollow distal tip to move off-axis of the elongate body to expose the distal cutting edge. The device can further include a reflective element positioned within the slot that can be configured to radially direct light from the optical fiber out of the elongate body. The distal end of the optical fiber can be less than 3 mm from the distal cutting edge. The optical fiber can be fixed to the slot, but otherwise be free to float within the cutting and imaging assembly and the drive shaft. The cutting and imaging assembly can be configured to rotate relative to the elongate body and the hollow distal tip. The cutting and imaging assembly can be configured to extend into the hollow distal tip to pack tissue into the hollow distal tip.

In general, in one embodiment, an atherectomy catheter device includes an elongate body, a hollow distal tip, a bushing, a cutting and imaging assembly, and a crescent-shaped balloon. The elongate body extends distally to proximally. The hollow distal tip extends from a distal end of the elongate body. The bushing is coupled to the hollow distal tip and is hinged at a side of the elongate body. The cutting and imaging assembly has a distal cutting edge and an imaging sensor. The crescent-shaped balloon is wrapped around portions of the elongate body, hollow distal tip, and bushing, while leaving the distal cutting edge exposed. The balloon is configured to urge the distal cutting edge against a vessel wall and occlude blood flow therearound.

This and other embodiments can include one or more of the following features. The balloon can be further configured to displace the distal tip relative to the elongate body to expose the distal cutting edge. A guidewire lumen can extend within the balloon for an entire length of the balloon. The imaging sensor can be an optical coherence tomography imaging sensor. Proximal or distal movement of the drive shaft can cause the hollow distal tip to move off-axis of the elongate body about the hinge point to expose the distal cutting edge.

In general, in one embodiment, an OCT imaging atherectomy catheter device having a plurality of imaging positions includes an elongate body, a hollow distal tip, and a rotatable cutting and imaging assembly. The elongate body extends distally to proximally. The hollow distal tip extends from a distal end of the elongate body and is hinged at a side of the elongate body. The rotatable cutting and imaging assembly is coupled to a rotatable and axially moveable drive shaft that extends distally to proximally within the elongate body and has an OCT imaging sensor that is proximally adjacent to a distal cutting edge. The rotatable cutting and imaging assembly is configured to panoramically image biological tissue surrounding the catheter through the hollow distal tip when the rotatable cutting and imaging assembly is positioned at a first position that is within the hollow distal tip. The rotatable cutting and imaging assembly is further configured to image a portion of the biological tissue surrounding the catheter and a displacement of the hollow distal tip relative to the elongate body from a second position that is proximal to the first position to indicate whether the distal cutting edge is exposed.

This and other embodiments can include one or more of the following features. The catheter can further include a first imaging window and a second imaging window. An angle between the first imaging window and the second imaging window can further indicate whether the distal cutting edge is exposed. The imaging sensor can be aligned with the first and second windows when in the second position. The device can further include a third imaging window. The cutting and imaging assembly can have a third position wherein the imaging sensor is aligned with the third imaging window. The OCT imaging sensor of the rotatable cutting and imaging assembly can include an optical fiber and a reflector within the rotatable cutting and imaging assembly. The distal tip can include a bushing at a proximal end. The bushing can be hinged to the elongate body.

In general, in one embodiment, an atherectomy catheter device configured to drive a rotatable cutting assembly against a vessel wall includes a flexible elongate body, a hollow distal tip, a rotatable cutting assembly, a first balloon, and a fulcrum balloon. The hollow distal tip extends from a distal end of the elongate body and is hinged at a side of the elongate body. The rotatable cutting assembly is coupled to a rotatable and axially moveable drive shaft that extends distally to proximally within the elongate body and has a distal cutting edge. The first balloon is near the distal end region of the elongate body and is configured to drive the distal cutting edge of the rotatable cutting assembly laterally into a vessel wall by pushing against the vessel wall in a first direction. The fulcrum balloon is positioned proximally to the first balloon and is configured to expand to push against the vessel wall in a direction that is opposite the first direction. The fulcrum balloon is less than 100 cm from the first balloon.

This and other embodiments can include one or more of the following features. The device can further include an optical coherence tomography (OCT) sensor on the cutting assembly proximally adjacent to the distal cutting edge. The first balloon can be opposite a lateral opening formed in a side of the catheter between the distal tip and the elongate body. The first balloon can be opposite the distal cutting edge of the rotatable cutting assembly when the distal tip bends away from the elongate body to expose the distal cutting edge. The fulcrum balloon can be less than 75 cm from the first balloon. The fulcrum balloon can be less than 50 cm from the first balloon.

In general, in one embodiment, an atherectomy catheter device includes an elongate body, a hollow distal tip, a bushing, a cutting and imaging assembly, and a plurality of jet channels within the bushing. The hollow distal tip extends from a distal end of the elongate body. The bushing is coupled to the distal tip and hinged at a side of the elongate body. The cutting and imaging assembly is coupled to a rotatable and axially moveable drive shaft that extends distally to proximally within the elongate body and includes a distal cutting edge. The plurality of jet channels within the bushing are directed distally and coupled with a fluid line extending though the elongate body. Fluid sent through the jet channels is configured to pack tissue cut by the distal cutting edge into the hollow distal tip.

This and other embodiments can include one or more of the following features. The plurality of jet channels can include two channels extending along an inner circumference of the bushing. The jet channels can be positioned to create a venturi effect at the distal end of the cutting and imaging assembly.

In general, in one embodiment, an atherectomy device includes an elongate body, a distal tip, a rotatable cutting and imaging assembly, an optical fiber, and a handle attached to the elongate body. The distal tip extends from a distal end of the elongate body and is hinged at a side of the elongate body. The rotatable cutting and imaging assembly is coupled to a rotatable and axially movable drive shaft that extends distally to proximally within the elongate body. The cutting and imaging assembly has an OCT imaging sensor. The optical fiber extends from the OCT imaging sensor and proximally through the drive shaft. The handle attached to the elongate body includes a cylindrical fiber holding chamber and an optical fiber coupling region. The cylindrical fiber holding chamber is at the proximal end of the catheter and is configured to rotate with the drive shaft and optical fiber.

The fiber holding chamber has an inner region into which the optical fiber extends. The optical fiber coupling region is configured to couple the optical fiber to a light source. The optical fiber and drive shaft are configured to move axially within the handle relative to the cylindrical fiber holding chamber and optical fiber coupling region. The optical fiber is configured to bend within the fiber holding chamber as the optical fiber and drive shaft move axially.

This and other embodiments can include one or more of the following features. The handle can further include a driveshaft tensioning spring configured such that, when the driveshaft is moved proximally, the spring can compress to apply a controlled tensile load on the driveshaft. The elongate body can further include a balloon connected thereto and a balloon inflation lumen extending along the elongate body. The handle can include an inflation chamber therein configured to connect to the balloon inflation lumen. The elongate body can be configured to rotate independently of the balloon inflation chamber.

BRIEF DESCRIPTION OF THE DRAWINGS

FIGS. 1A-1C illustrate a side perspective view of the end of an exemplary atherectomy device having an offset hinged region, a bushing, and an imaging/cutting assembly with a neck region that engages the bushing. FIG. 1B shows the catheter with the housing for the hollow distal tip removed. FIG. 1C shows the catheter of FIG. 1B with the proximal connector to the outer sleeve of the elongate body removed, showing the bushing and rotatable drive shaft.

FIGS. 4B, 4C and 4D each show the catheter of FIG. 4A with various components removed to allow description of internal parts.

FIGS. 7A-7D show perspective, side, top and front views, respectively of a bushing for an atherectomy device.

FIG. 8A shows a panoramic OCT image of a blood vessel through the nosecone of an atherectomy catheter, as identified by the arrow in FIG. 8B.

FIG. 9A shows a panoramic OCT image of a blood vessel taken with an atherectomy catheter through the cutting window(s) when the nosecone is closed and the cutter is in a passive position, as identified by the arrow in FIG. 9B.

FIGS. 11A and 11B show another embodiment of an atherectomy catheter having a cutter engaging distal surface that is normal to the longitudinal axis of the catheter. FIG. 11A shows a cross-section of the catheter while FIG. 11B shows a side view of the bushing.

FIGS. 12A and 12B show another embodiment of an atherectomy catheter having a cutter engaging distal surface that is at an angle relative to the longitudinal axis so as to provide only a point of contact with the distal surface of the cutter. FIG. 12A shows a cross-section of the catheter. FIG. 12B shows a side view of the bushing.

FIGS. 15A-15D show examples of tips that may be used for occlusion-crossing catheters.

FIGS. 18A-18D show perspective, side, top and front views, respectively, of a bushing for an atherectomy device.

FIG. 18E is a bottom view of the bushing of FIGS. 18A-18D, while FIGS. 18F and 18G are back and sectional views (taken through the midline of the long axis, G' in FIG. 18D), respectively.

FIG. 18H is a perspective view of the sectional view shown in FIG. 18G.

FIGS. 22A-22H illustrate relative movements of the bushing and cutter. FIGS. 22A, 22C, 22E, and 22G show perspective views in which the bushing is shown partially transparent as the cutter is exposed by pulling it proximally. FIGS. 22B, 22D, 22F, and 22H show corresponding respective end front-end view of the assemblies of FIGS. 22A, 22C, 22E, and 22G.

DETAILED DESCRIPTION

Figure 2A:
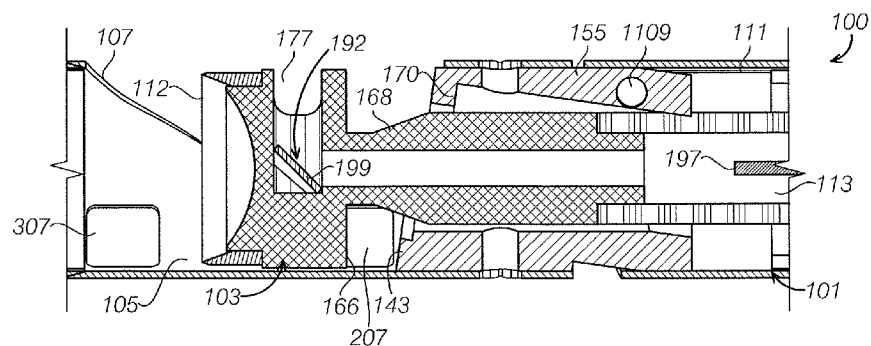
FIG. 2A shows a sectional view though an atherectomy catheter such as the one shown in FIGS. 1A-1C, with the distal tip in-line with the elongate (proximal) body region.

Described herein are atherectomy catheters and occlusion-crossing catheters. In particular, described herein are catheters having distal tip that may be deflected (e.g., to expose a rotating cutter) in a mechanically advantageous manner by use of a multi-channel bushing having a radially offset hinge point or points and a pair of flange points. The operation of the rotating cutter head within the multi-channel bushing may be actuated by the drive shaft by pushing and pulling, and may translate axial motion of the drive shaft into radial bending/movement of the tip to create a deflection requiring relatively little force and/or lateral deflection.

Atherectomy Catheters

The atherectomy catheters described herein can include a catheter shaft with a drive chassis on the end. The drive chassis includes a stout torque coil ("imaging torqueing coil"/drive shaft) for rotating an imaging element, a cutter, and an imaging optical fiber in the center of the torque coil. Both the imaging elements and the cutter can be part of a head that rotates with the driveshaft. The head can rotate in a single direction (e.g., clockwise). The head can further slide distally/proximally by pushing or pulling the torque coil/drive shaft. As a result of the movement of the driveshaft, a nosecone configured to hold tissue can be displaced. In some embodiments, the nosecone can open and close using an off-axis hinge. In other embodiments, a cam member and cam slot can be used to open and close the nosecone.

FIGS. 1A-3 show an example of an atherectomy catheter 100 including a nosecone that deflects to expose a cutter. The atherectomy catheter 100 can include a catheter body 101 having an outer shaft 111, a cutter 103 at a distal end of the catheter body 101, and a nosecone 105 at a distal end of the catheter body 101. The nosecone 105 can further include a cutting window 107 through which the cutting edge 112 of the cutter 103 can be exposed. The nosecone 105 can be configured to deflect away from the longitudinal axis of the catheter body 101 about a hinge point 1109, as described further below. This deflection can expose the cutter 103 through the cutting window 107 and/or radially push the cutter 103 into a wall of the vessel in which the atherectomy catheter is inserted.

Referring to FIGS. 1A-2C, the cutter 103 can be positioned between the catheter body 101 and the nosecone 105 via a bushing 155. In some embodiments, the cutter 103 can be an annular cutter with a sharp distal edge 112. The cutter 103 can be attached to a drive shaft 113 configured to rotate the cutter 103. As described in greater detail below, the bushing 155 shown in FIGS. 1A-3 is just one example of a bushing. Other examples (see, e.g., FIGS. 7A-7G and 18A-18G) are shown and described below, and include different or alternative features that may be incorporated into any of these variations described herein.

Figure 2B:
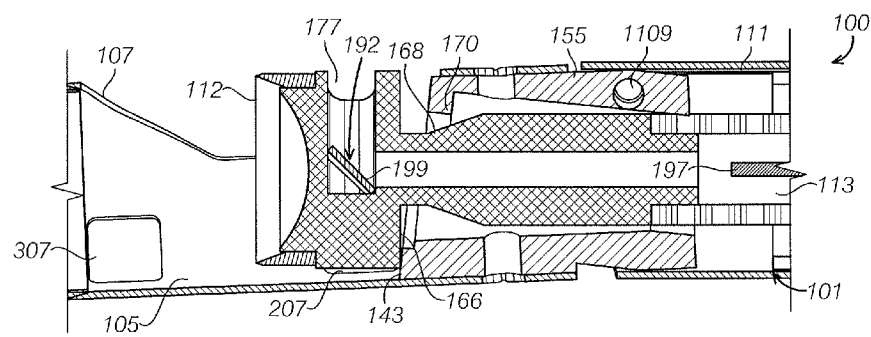
FIG. 2B shows the catheter of FIG. 2A as the tip beings to be displaced downward.

Further, referring still to FIGS. 2A-2B, the atherectomy catheter 100 can include an imaging element 192, such as an OCT imaging element, within the cutter 103 and proximal to the cutting edge 112 of the cutter 103. The imaging element 192 can include an optical fiber 197 that runs substantially on-axis through the center of the elongate body, such as through the driveshaft 113, to transmit the OCT signal. Further, the optical fiber 197 can run straight throughout the catheter body 101 without bending. The optical fiber 197 can be attached at the distal end to the cutter 103, such as in a slot 177 in the cutter 103. The slot can have a length that extends at least to the center of the cutter 103 so as to allow the optical fiber 197 to remain on-axis without a bend through the length of the catheter body 101 and the cutter 103. Aside from the attachment to the cutter 103, the optical fiber 197 can be otherwise be free to float within the catheter body or drive shaft 113. In other embodiments, the optical fiber 197 can be attached to the drive shaft 113 along the length thereof.

Figure 2C:
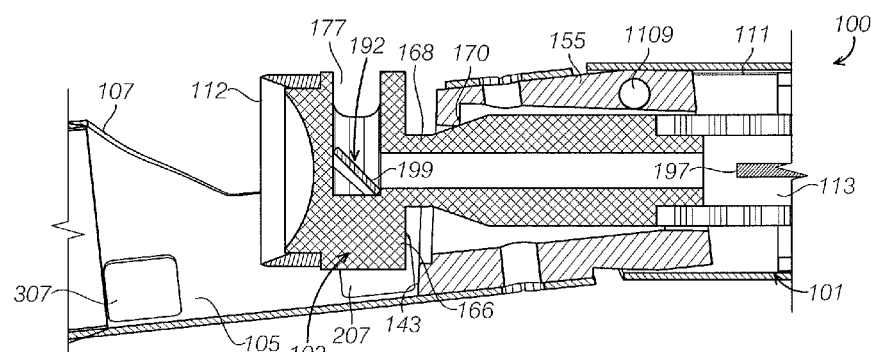
FIG. 2C shows the catheter of FIG. 2A with the tip fully displaced downward, exposing the cutting edge of the cutting/imaging assembly.

As shown in FIGS. 2A-2C, the imaging element 192 can include a reflective element 199, such as a mirror. The reflective element 199 can be located within the slot 177 in the cutter 103 to radially direct light from the optical fiber 197 into the adjacent tissue (through the cutter window 107). The reflective element 199 can be oriented at an angle relative to the axis of the optical fiber 197, such as at a 35-55 degree angle, e.g. 45 degree angle, to reflect light into the tissue. The distal end of the optical fiber 197 can be located less than 3 mm from the cutting edge, such as less than 1 mm from the cutting edge, such as less than 0.5 mm. By having the imaging element 192 close to the cutting edge, the resulting image can advantageously align with the portions of the vessel being cut.

In use, the outer shaft 111 can be configured to be turned, such as turned manually, to position the cutter window 107, cutter 103, and/or the imaging element 192 toward the desired location. The driveshaft 113 can then be rotated to rotate the cutter 103 and the imaging elements 197. Rotation of the cutter can provide cutting due to the rotational motion of the cutting edge and provide the rotation necessary to image the vessel wall via the imaging element. The drive shaft can be rotated at up to 2,000 rpm, such as approximately 1,000 rpm in a single direction, though rotation in both directions or at higher or lower speeds is possible.

Referring to FIGS. 2A-2C, the drive shaft 113 can further be configured to translate axially in the proximal and/or distal directions. Such axial movement of the drive shaft 113 can open and/or close the nosecone 105 about the hinge point 1109 (e.g., a pin in the bushing 155) to expose or conceal and protect the cutting edge 112 of the cutter 103. For example, the bushing 155 can include an inner flange 170 that extends radially inwards. The inner flange 170 can be positioned distal to the hinge point 1109. The bushing 155 can further include sloped outer distal surface 143 that angles radially inward from the distal end to the proximal end. Finally, the cutter 103 can include a proximal edge 166 and a tapered neck 168 that gets narrower from the driveshaft 113 to the head of the cutter 103. The interaction of these various elements can open and close the nosecone 105.

In one embodiment, proximal retraction of the drive shaft 113 opens the nosecone 105 to expose the cutter. For example, as the driveshaft 113 is pulled proximally, the proximal edge 166 of the cutter 103 is forced against the sloped distal surface 143 of the bushing 155. Because the sloped distal surface 143 angles radially inward from the distal end to the proximal end, the cutter 103 forces the bushing 155, and thus the nosecone 105, to deflect away from the longitudinal axis of the catheter body 101, thereby opening the nosecone 105 (see the transition from FIGS. 2A to 2B and 2B to 2C). The cutting window 107 can have an opening that is larger than the diameter of the cutter 103 and cutting edge 112 to allow the cutter 103 to protrude out of the nosecone 105 when the nosecone 105 is deflected.

In one embodiment, distal movement of the drive shaft 113 closes the nosecone 105. For example, as shown in FIGS. 2A-2C, when the drive shaft 113 is pushed distally, the tapered neck 168 of the cutter 103 will correspondingly move distally. The distal movement of the tapered neck 168 causes the inner flange 170 of the bushing 155 to drag along the widening edges of the tapered neck 168, thereby lifting the bushing 155, and correspondingly, closing the nosecone 105 (see the transition from FIGS. 2C to 2B and 2B to 2A). Because the hinge point is proximal to the inner flange 170, a mechanical advantage is achieved that allows for complete closing of the nosecone.

FIGS. 7A-7D show close-ups of one variation of a bushing 155'. As shown, the bushing 155' can include two intersecting channels 721, 723 configured to hold the necked portion 168 of the imaging subassembly therein when the nosecone is in the open configuration (channel 723) and the closed configuration (channel 721). Channel 721 extends through a long distal to proximal axis of the bushing 155' while channel 723 extends at an angle relative to channel 721 and overlaps therewith. The bushing 155' can further include a hinge channel 745 formed through a top peripheral region of the bushing 155 so as to provide the pivot point 1109. The hinge channel 745 can be transverse to the channel 721.

Any of the bushings described herein may be referred to as multi-channel bushings, because they may include at least two overlapping channels, in which one of the channels is at an angle relative to the other.

For example, any of the apparatuses described herein may be atherectomy catheter devices that include a multi-channeled bushing. As shown and described in FIGS. 1A-2C, a catheter may include an elongate body 101 with a tip 105 (e.g., nosecone, distal tip, etc.) extending from a distal end of the elongate body, a drive shaft 113 extending within the elongate body, and a bushing pivotally connected to the elongate body and/or tip.

In general, a bushing 155' (as shown in FIGS. 7A-7G) may include a bushing body 156. The bushing body may be any appropriate material, including polymers (e.g., plastics, Polyether ether ketone, polyethylene, polypropylene, polystyrene, polyester, polycarbonate, polyvinyl chloride, polyethersulfone, polyacrylate, polysulfone, polyetheretherketone, thermoplastic elastomers, silicone, parylene, fluoropolymers, etc.), metals (including alloys), and ceramics.

The bushing typically includes one or more (preferably two) hinge points 745 on a side of the bushing body. In FIGS. 7A-7G the hinge points are a hinge channel that extends perpendicular to the elongate axis of the bushing body through a region that is off-axis, meaning it is offset from a midline along a distal-to-proximal axis of the bushing body. The hinge point in this example is part of a hinge channel formed through a top peripheral region of the bushing body (extending transverse to the long axis of the bushing, including transverse to the two channels 721, 723 extending distally to proximally).

As mentioned, the bushing body may include a first channel 721 extending proximally to distally through the bushing body and a second channel 723 extending proximally to distally through the bushing body. The first and second channels overlap. In general, the first channel may have a diameter that is greater than or equal to the diameter of the second channel.

Figure 7F:
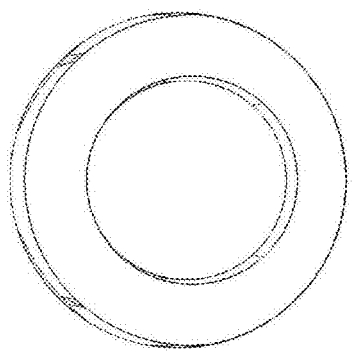
FIG. 7F is a back view.
Figure 7E:
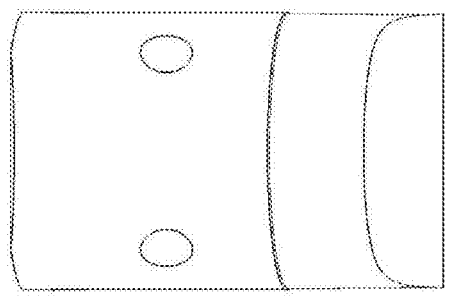
FIG. 7E is a bottom view.
Figure 7G:
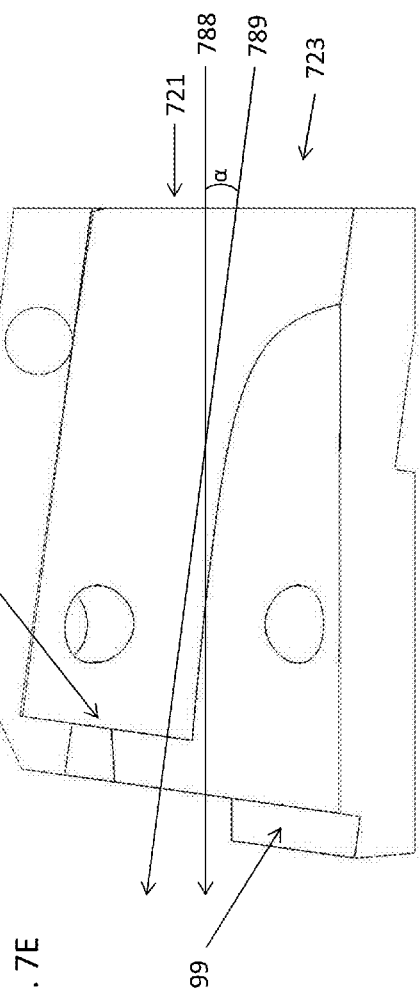
FIG. 7G is a sectional longitudinal view.

As mentioned, the long axis 788 of the first channel may extend through the bushing, proximally to distally. The long axis 789 of the second channel also extends through the bushing proximally to distally, overlapping with the first channel, as shown in FIG. 7G. In the longitudinal section (G) through the bushing shown in FIG. 7C, the first channel 721 overlaps with the second channel 723, and the angle ($\alpha$) between the first and second channels is typically between about 1° and about 45° (e.g., between a lower angle of 2°, 3°, 4°, 5°, 7°, 10°, 12°, 15°, 17°, 20°, etc.) and an upper angle of 15°, 20°, 22°, 25°, 30°, 35°, 40°, 45°, 50°, 60°, etc., where the lower angle is always less than the upper angle).

The bushing may also include a first opening 775 at a distal end of the bushing body into the first channel (visible in FIG. 7A), and a second opening 776 at the distal end of the bushing body into the second channel, wherein the first and second openings overlap.

In general, any of these apparatuses may also include a cutter. The cutter 103 may generally include a distal cutting head 119 with a cutting edge 112, an elongate cylindrical body 123, and a neck region 168 extending between the distal cutting edge and the elongate cylindrical body, wherein the drive shaft is coupled to the elongate cylindrical body.

FIGS. 18A-18H and 19 illustrate another variation of a bushing that may be used with any of the atherectomy catheter devices described herein. As mentioned, the atherectomy catheters described herein may generally include an elongate body (not shown) to which a multi-channeled bushing is attached. The bushing typically makes the bending joint between the distal tip region and the more proximal elongate body or shaft. As described above, an internal torque shaft (which may be woven, or the like) may be connected (e.g., by soldering, crimping, etc.) to the proximal end of a cutter. The cutter may be positioned within the bushing, as will be described in greater detail with reference to FIGS. 21-22G, below. The bushing may be attached via hinge pin to the proximal elongate body, and in particular, the off-axis or off-center hinge point on the side of the bushing. Multiple hinge pins may be used or a single hinge pin may be used. The pin may secure the bushing to the covering forming the elongate body within which the drive shaft extends. The distal end of the proximal shaft may include an adapter to which the pin (hinge pin) may be attached, e.g., by welding, allowing the bushing to rotate about the off-center/off-axis hinging region. The distal end of the bushing may be connected to the nosecone forming the distal tip of the apparatus. The nosecone may be hollow to allow packing of cut material within it. The bushing may be connected to the nosecone by any appropriate manner, including crimping and/or welding and/or adhesive, etc.

Any of the exposed edges, such as the edges of the bushing, adapter, nosecone, etc. may be radiused (e.g., have a radiused edge) to prevent undesirable damage to the tissue.

Figure 19:
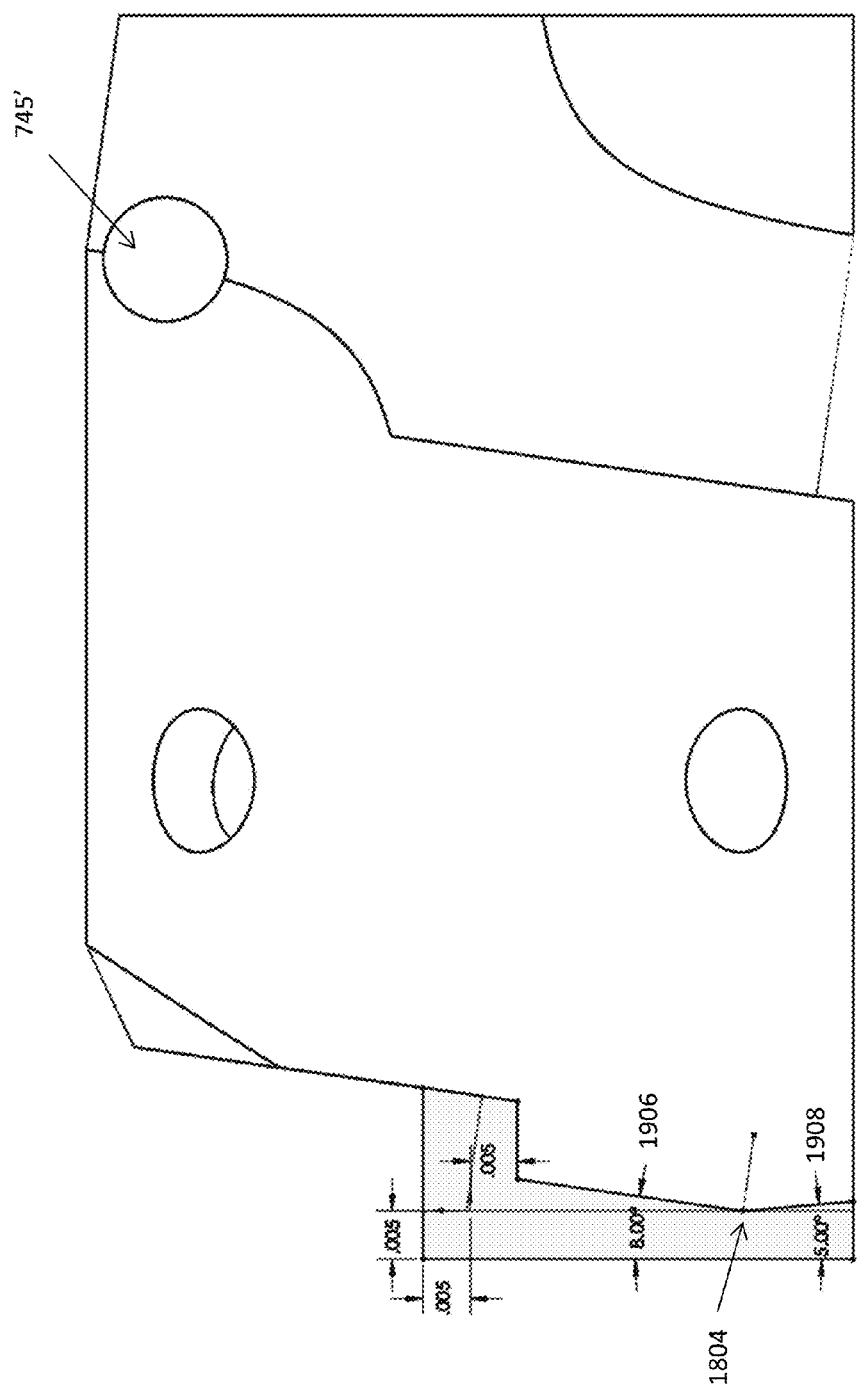
FIG. 19 is a side view, showing exemplary dimensions, of one variations of a bushing such as the bushing shown in FIGS. 18A-18H.
Figure 20B:
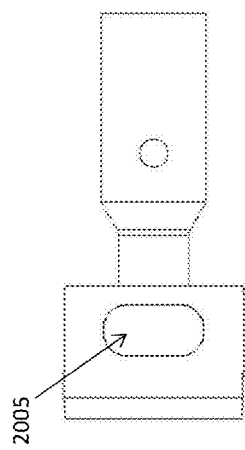
FIGS. 20A-20D illustrate perspective, top, side and bottom views, respectively, of an exemplary cutter having a distal cutting head with a cutting edge, an elongate cylindrical body, and a neck region.
Figure 20C:
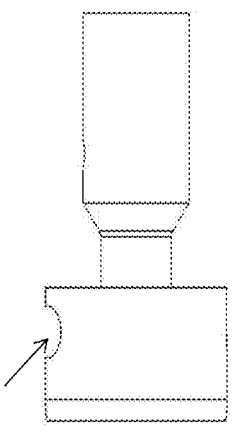
Figure 20D:
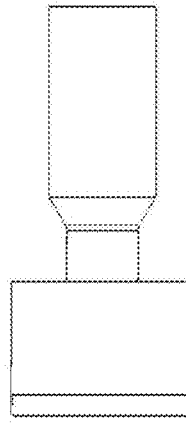
Figure 20A:
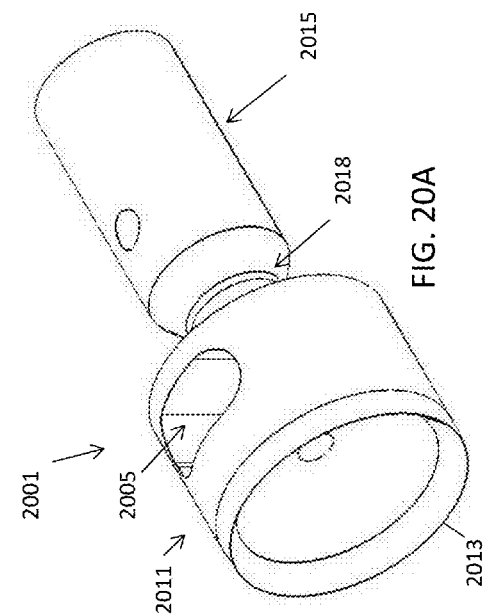

In any of the bushings described herein, including the example shown in FIGS. 18A-19, the bushing may include a bushing body, 156', a hinge point (or hinge channel 745' forming one or more hinge points) on a side of the bushing body, a first channel 721' having a first opening 775') extending proximally to distally through the bushing body, and a second channel 723' (having a second opening 776' that is overlapping, but not coextensive with the first channel opening) extending proximally to distally through the bushing body. The second channel generally has a diameter that is less than a diameter of the first channel, and the second channel may be angled between 1° and 45° relative to the first channel, as illustrated in FIG. 18G. The angle ($\alpha$) between the long axis of the first channel 788' relative to the long axis of the second channel 789' is between 1° and 45° (shown in FIG. 18G as approximately 15°).

As shown in FIGS. 20A-20D, any of these apparatuses may include a cutter 2001 having a distal cutting head 2011 with a cutting edge 2013, an elongate cylindrical body 2015, and a neck region 2018 extending between the distal cutting edge 2013 and the elongate cylindrical body 2015. As mentioned, the drive shaft may be coupled to the elongate cylindrical body. The cutter may also be adapted to form the OCT lens/imaging window, as described herein. For example, in FIGS. 20B-20D, the cutter head includes a window region 2005 that is continuous with an internal passage through the cutter, into which an OCT lens may be formed at the distal end of an optical fiber. The lens may include a mirror (not shown) and/or OCT-transparent epoxy or resin holding the distal end of the fiber in position (not shown).

The distal-most edge of the bushing may be straight or curved line 1804 that is formed at the flange region so that the bushing may contact the back of the cutter at a point or line. This will be illustrated below with reference to FIGS. 2A-22H. For example, FIG. 18B illustrates a profile including the distal edge of the bushing. In this example, the distal end of the bushing includes a distal-most flange or rim 143 that forms a line or point 1804 between two angled surfaces.

The surface extending on one side (e.g., upper surface 1906) of this line 1804 has an angle relative to the long axis of the first channel through the bushing that is approximately the same as or greater than the angle that the nosecone is deflected relative to the distal end of the elongate body of the apparatus when the cutter is exposed. This is illustrated, for example in FIG. 19, which includes exemplary dimensions (in inches and degrees). In FIG. 19, the distal most edge 1804 is formed by an angled upper surface 1906 of the partial flange and the oppositely-angled lower surface 1908 of the partial flange. The angle of this upper surface relative to the long axis of the first channel through the flange is shown as 8° degrees from the perpendicular of the long axis. Similarly, the angel of the lower surface 1908 relative to the long axis of the first channel through the flange is 5° degrees from the perpendicular of the long axis, as shown. This flange region 1809 extends around just the bottom of the distal end of the bushing, and may be sized to hold the cutter head of the cutter within the bushing distal end when the cutter is retracted fully proximally.

Because of the configuration of the bushing, including in particular the features described above, the bushing may be actuated to move tilt the distal tip of the catheter in-line with the elongate body or at an angle to the elongate body, as shown in FIGS. 2A-2C. In this example, distal movement of the drive shaft extends the cylindrical body of the cutter within the first channel of the bushing and drives the tip about the hinge point to axially align the tip with the elongate body and at least partially cover the cutting edge. In addition, proximal movement of the drive shaft extends the neck region of the cutter within the second channel of the bushing and drives the tip about the hinge point to angle the tip relative to the elongate body and at least partially expose the cutting edge. Alternatively or additionally, pushing the drive shaft distally may drive the neck region against the inner flange 798 (visible in the section shown in FIG. 7G), while pulling the drive shaft proximally may drive the proximal-facing (back, proximal side) of the cutter against an outer flange 143, which may include a sloped distal surface.

Figure 21:
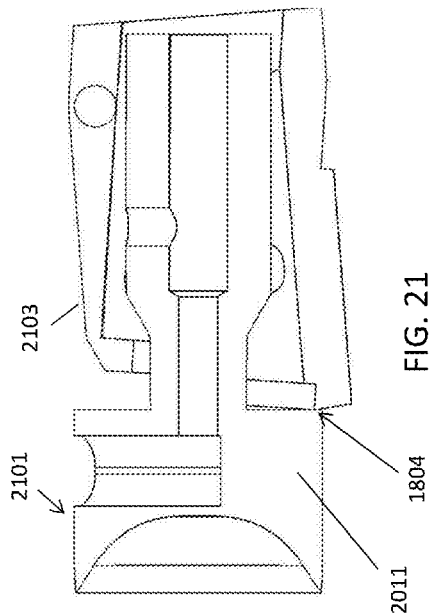
FIG. 21 is a sectional view through the long axis of the cutter engaging a bushing. In practice, the bushing may be connected to the proximal body portion of the tip of the atherectomy device (not shown) and pivotally connected to the shaft (proximal end) of the atherectomy device, and the cutter may be secured at the distal end to a torque shaft (not shown in FIG. 21).
Figure 22A:
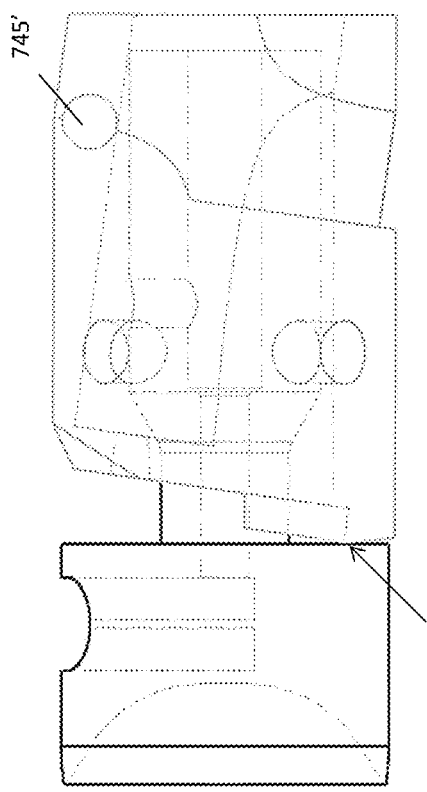
Figure 22C:
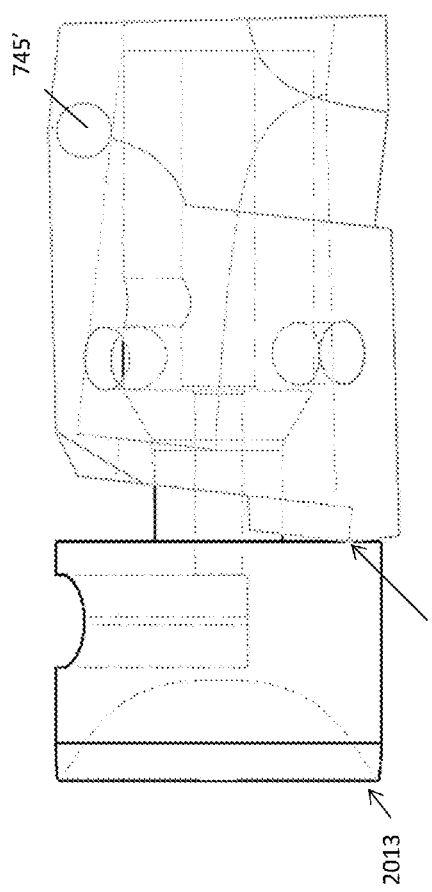
Figure 22B:
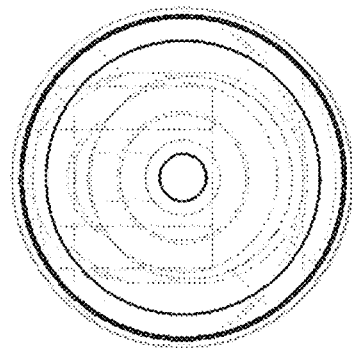
Figure 22D:
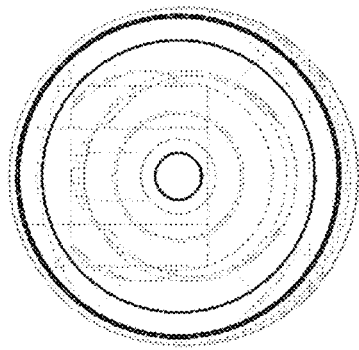

FIG. 21 illustrates one example of a cutter engaged 2101 with a bushing 2103. The bushing in this example is similar to the bushing shown in FIGS. 18A-18H. The bushing engages with the cutter head 2011 only at the distal-most point or line 1804 of the bushing. In this example, the bushing is a PEEK bushing, and the cutter is metal. In FIG. 22A, the back of the cutter head (rear of the cutter face) contacts the distal-most (leading) edge or point of the bushing 1804, when the cutter is pulled back to deploy the cutter and expose it for cutting. Pulling back on the torque shaft forces this distal/leading edge of the bushing against the back of the cutter, which may be rotating. In FIG. 22A, the tip (nose cone) of the atherectomy catheter is in the same line as the elongate axis, and the cutter is flush or nearly flush with the outer wall of the distal end of the catheter, preventing cutting within the vessel. As shown in FIG. 22B, the cutter and bushing are in line. At the start of pull-back of the cutter, e.g., by pulling the torque shaft, a moment is created that begins to tilt the bushing downward, as shown in FIG. 22C. In FIG. 22C, the leading edge of the bushing begins to ride up the rear face of the cutter, and the bushing (to which the nosecone is fixedly attached distally) beings to rotate about the off-axis hinge point 745' driving the nosecone (not shown) down, and beginning to expose the cutter's cutting edge 2013, which is also visible in the end view shown in FIG. 22D. This process continues, as shown in FIG. 22E; the moment arm between the leading edge 1804 of the bushing and the hinge point(s) 745' is sufficiently large so that the force applied by driving the cutter against the leading edge forces the nosecone down, until, as shown in FIG. 22G, the cutter head drops into the partial flange formed by the bushing, and is securely held in this seating position, as shown. Thus, the downward moment is applied so that the leading edge of the bushing rides along the rear face of the cutter until the cutter is seated. FIGS. 22G and 22H show the final position of the cutter (cutter head) seated on the ledge of the bushing.

To reverse this, the distal movement of the drive shaft extends the cylindrical body of the cutter within the first channel of the bushing and drives the tip (nosecone) about the hinge point to axially align the tip with the elongate body and at least partially cover the cutting edge. Similarly, to again deflect the nosecone, proximal movement of the drive shaft will again extend the neck region of the cutter within the second channel of the bushing and drives the tip about the hinge point to angle the tip relative to the elongate body and at least partially expose the cutting edge.

Other mechanisms of opening and closing the nosecone are possible. For example, as shown in FIGS. 4A-4D, in one embodiment, a catheter 200 (having similar features to catheter 100 except the opening and closing mechanisms) can include a cam slot 228 in the bushing 155 that angles toward the cutting window 107 from the proximal end to the distal end. Further, a cam member 290 can be attached to the cutter 103 and configured to extend through the cam slot 228. Thus, as the driveshaft 113, and thus cam member 290, are pushed distally, the cam member 290 will move within the angled cam slot 180. The movement of the cam member 290 within the angled cam slot 180 causes the bushing 155, and thus the nosecone 150, to drop down. Conversely, to close the nosecone, the driveshaft 113 can be pulled proximally, thereby causing the cam member 290 to ride within the cam slot 228 and pull the bushing 155' back into line with the elongate body 101.

Another mechanism of opening and closing a nosecone of an atherectomy catheter 400a,b is shown in FIGS. 11A-11B and 12A-12B. The catheter 400a,b can have the same features as catheter 100 except that the outer distal surface 443a,b of the bushing 455a,b can be either normal to the longitudinal axis of the device (such that the angle α is 90 degrees), as shown in FIG. 11B or slanted radially outward from the distal end to the proximal end (such that the angle α is greater than 90 degrees and the angle with the longitudinal axis is less than 90 degrees), as shown in FIG. 12B. In the embodiment of FIGS. 12A-12B, an angled space is provided between the proximal edge 166 of the cutter and the distal surface 443b such that the only point of contact is an inner radial edge 444 of the bushing 455b. The catheter 400a will open and close similarly to as described with respect to catheter 100. However, the catheter 500b will open slightly differently in that only the inner-most radial edge 444 will interact with the proximal edge 166 of the cutter 103, as opposed to the entire surface 443, when the driveshaft 113 is pulled proximally. Such a configuration can advantageously reduce friction while opening the nosecone 105. In some embodiments, the proximal edge 166 can be angled with respect to a longitudinal axis of the catheter; in such cases, the opposing surface 443 of the bushing 455 can be either parallel to or angled (acute or obtuse) with respect to the proximal edge 166.

Figure 3:
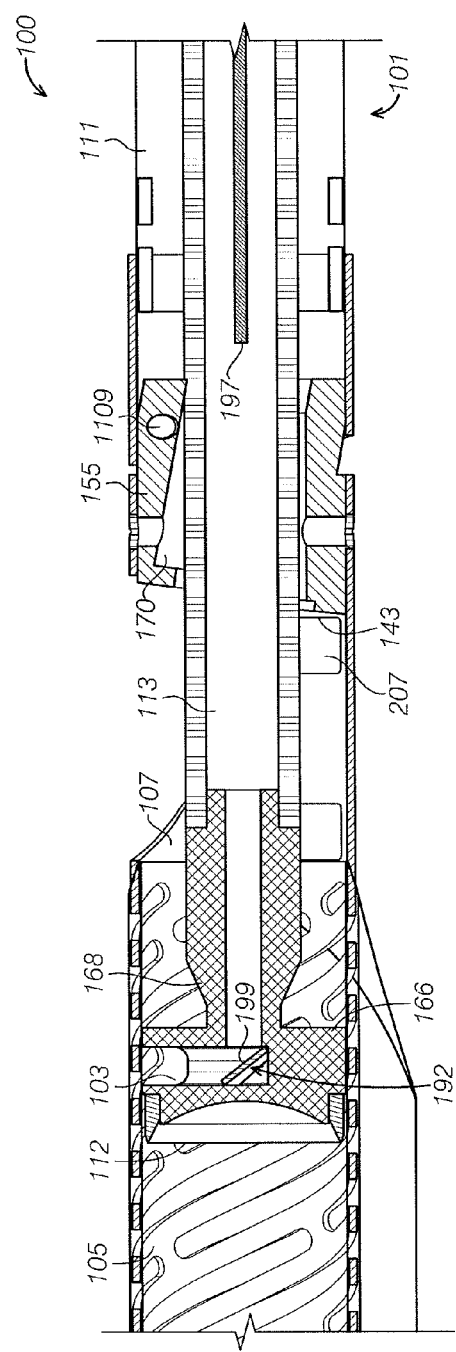
FIG. 3 shows a catheter with the cutting/imaging assembly extended distally into the distal tip region.
Figure 4A:
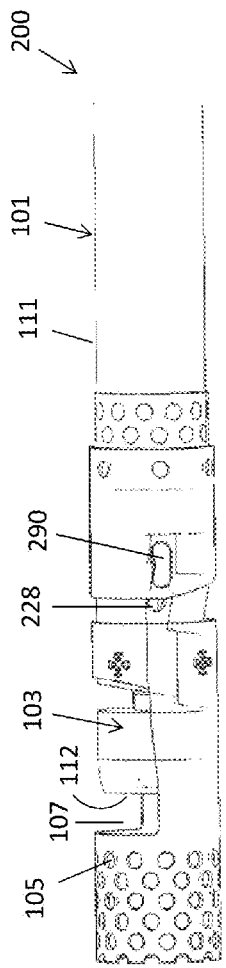
FIGS. 4A-4D illustrate another variation of an atherectomy catheter.
Figure 4B:
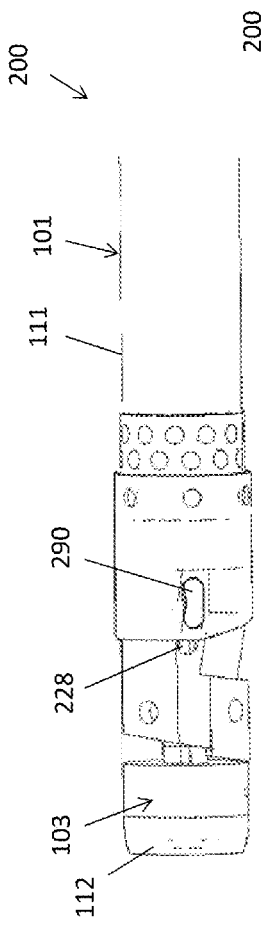
Figure 4C:
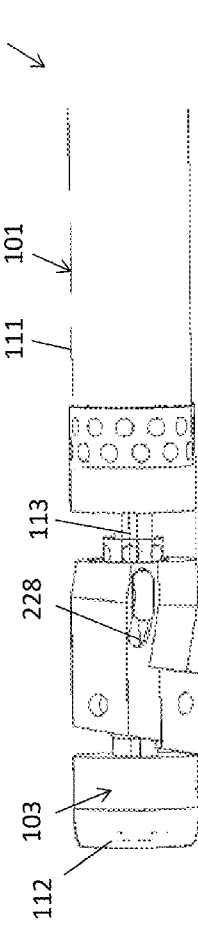
Figure 4D:
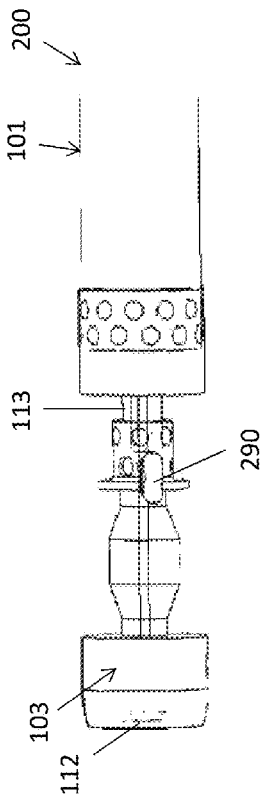

As shown in FIG. 3, the atherectomy catheter 100 (or 200 or 400) can further include a mechanism for packing tissue into the nosecone, such as by moving the drive shaft axially. In one embodiment, movement of the drive shaft 113 distally closes the nosecone 105. Moving the drive shaft 113 further distally will move the cutter 103 into a passive position (i.e., against a distal edge of the window 107) where the cutter 103 can be protected by the edge of the window 107 to avoid undesired cutting of the vessel during use. Moving the drive shaft 113 further distally will move the cutter 103 into the nosecone 105, thus packing tissue with a distal face of the cutter 103, as shown in FIG. 3. The cutter 103 can move more than 0.5 inches, such as more than 1 inch or more than 2 inches into the nosecone 105 to pack the tissue. In some embodiments, the nosecone 105 is formed of a material that is OCT translucent (e.g., non-metallic) so that panoramic OCT images can be taken therethrough.

Figure 16A:
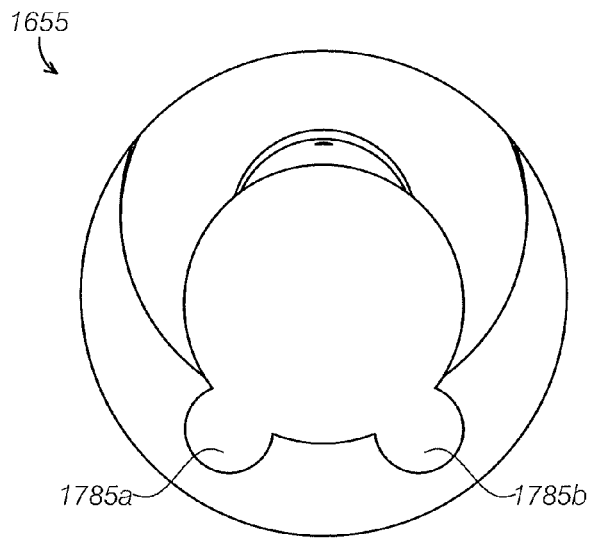
FIGS. 16A and 16B show a bushing having jet channels therethrough to assist in packing of tissue into the nosecone of an atherectomy catheter.
Figure 16B:
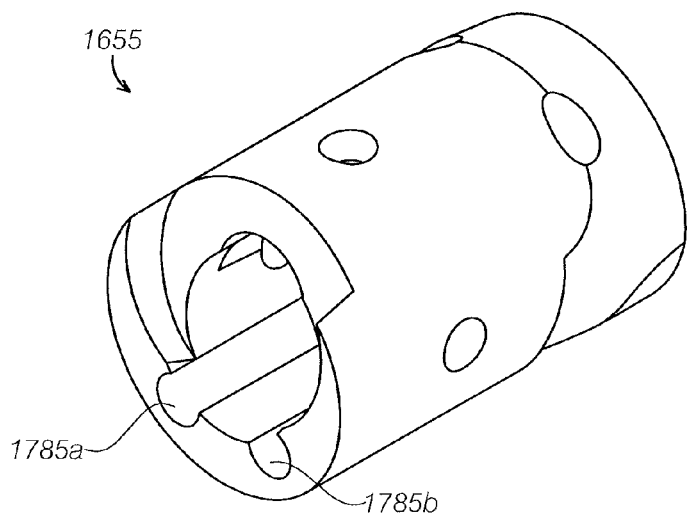

Referring to FIGS. 16A-16B, in some embodiment a bushing 1655 can include all of the features of the bushings described above, but can additionally include jet channels 1785a,b cut into the inner circumference thereof and extending from the proximal end to the distal end. The jet channels 1785a,b can connect a fluid line within the elongate body 101 to the nosecone 105. Fluid flowing through the jet channels 1785a,b can increase speed and thus provide enough force to pack cut material into the nosecone and clear the imaging region within the nosecone. Further, the jet channels can create a venturi effect at the distal end of the bushing 1655, which can suck material into the nosecone and/or away from the imaging/cutting head and/or the distal end region of the elongate body.

In one embodiment, the atherectomy catheter 100 (or 200 or 400) includes a guidewire lumen in the nosecone 105, such as a monorail, for use in guiding the catheter. Advantageously, the guidewire lumen can be used as a marker during imaging.

In some embodiments of atherectomy catheters 100, 200, or 400, there can be one or more small imaging windows 207, 307 in the nosecone 105 opposite to the cutting window 107, as shown in FIGS. 1A and 2A-2C. These additional imaging windows 207 can provide more of a 180 degree view during imaging. Further, one set of windows 207 can be more proximal and configured to be axially aligned with the cutter 103 and the imaging element 192 when the nosecone is opened while the other set of windows 307 can be more distal and configured to be axially aligned with the cutter 103 and the imaging element 192 when the nosecone is closed and the cutter 103 is in the passive position. In some embodiments, the imaging windows 307, 207 have different shapes from one another to further help identify cutter position in the resulting OCT images.

Referring to FIGS. 8A-11B, the OCT image catheter with the device will vary depending upon the placement of the imaging device in the three different configurations (nosecone open, nosecone closed with cutter in cutting position, nosecone closed with cutter in packing position). Accordingly, a user can identify, simply by looking at the imaging display, whether the nosecone 105 is displaced and whether the cutter 103 is in the cutting or packing position.

For example, FIG. 8A shows a panoramic image 800 of a surrounding vessel when the cutter 103 (and, correspondingly, the imaging sensor) is in the cutting position, as shown in FIG. 8B. The wall of the nosecone 105 is displayed as the circular feature 808 in the image 800. Further, because the nosecone 105 is made of a clear material, the vessel tissue 806 can be imaged even through the nosecone 105. As can be seen in image 800, a 180 degree view of the tissue 806 can thus be obtained. The circular artifact 803 in the image (and here, the radial line 801) correspond to a guidewire and/or guidewire channel running alongside the nosecone 105.

In contrast to image 800, FIG. 9A shows a panoramic image 900 of a surrounding vessel when the cutter 103 is in the passive position and the nosecone 105 is closed, as shown in FIG. 9B. A 180 degree view of the vessel tissue 906 is shown on the right side of the image (taken through window 107) while the closed nosecone 909 is shown on the left side of the image (the lines 909a,b correspond to the bushing wall). The space 913 between the lines 909a,b through which tissue 906 can be seen on the left side of the image is taken through the additional window 307 in the bushing. Further, the distance between the arrows in image 900 indicates that the distal tip is "closed" (and close therefore close to the midline of the catheter).

Figure 10A:
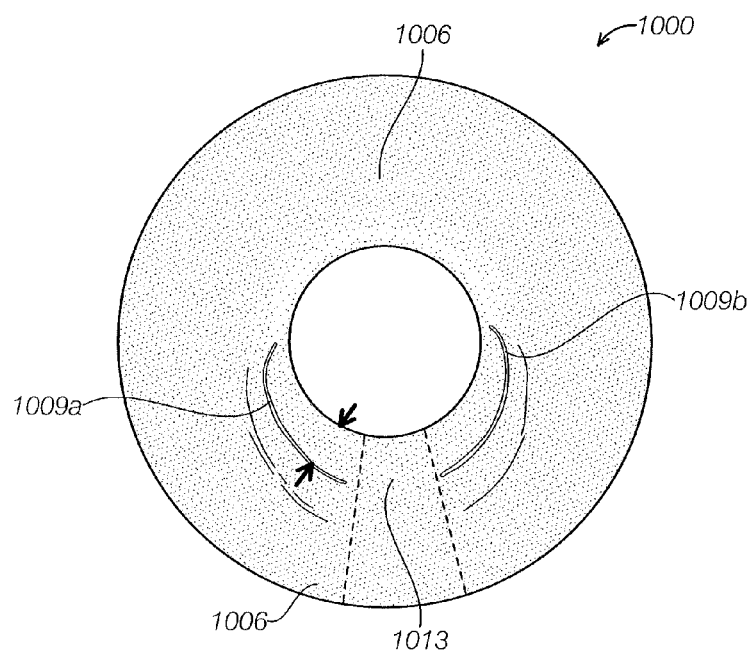
FIG. 10A shows a panoramic OCT image of a blood vessel taken with an atherectomy catheter through cutting window(s) when the nosecone is open, as identified by the arrow in FIG. 10B.
Figure 10B:
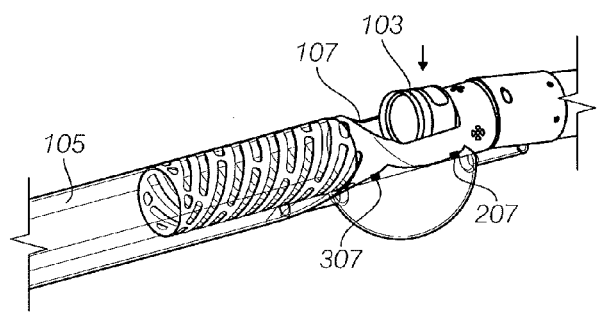

Finally, in contrast to image 900, FIG. 10A shows a panoramic image 1000 of a surrounding vessel when the cutter 103 is in the cutting position and the nosecone 105 is open, as shown in FIG. 10B. The vessel tissue 1006 (taken through window 107) is shown on the right side of the image while the closed nosecone 1009 is shown on the left side of the image (the lines 1009a,b correspond to the bushing wall). The space 1013 between the lines 1009a,b through which tissue 1006 can be seen is taken through the window 207. A comparison of the relative distance between the arrows in FIGS. 9A and 10A shows an increased distance between the catheter body and the nosecone, thereby suggesting to the operator that the nosecone 105 is in an open position. Further, in some embodiments, when the nosecone is open or closed, the image resulting from the window 207/307 will look different due to the angle change between the windows 207/307 and the imaging element 297 and/or the different shape of the windows 207/307.

In one embodiment, the atherectomy catheter 100 (or 200 or 400) includes a flush port close to the cutter 103. The flush port can be used to deliver flushing fluid to the region of imaging, thereby improving image quality. In some embodiments, the flushing can be activated through a mechanism on the handle of the device. The fluid can, for example, be flushed in the annular space between the catheter body 101 and the driveshaft 113. Further, in embodiments with jet channels in the bushing, the annular space can connect to the jet channels to provide fluid thereto.

Figure 6:
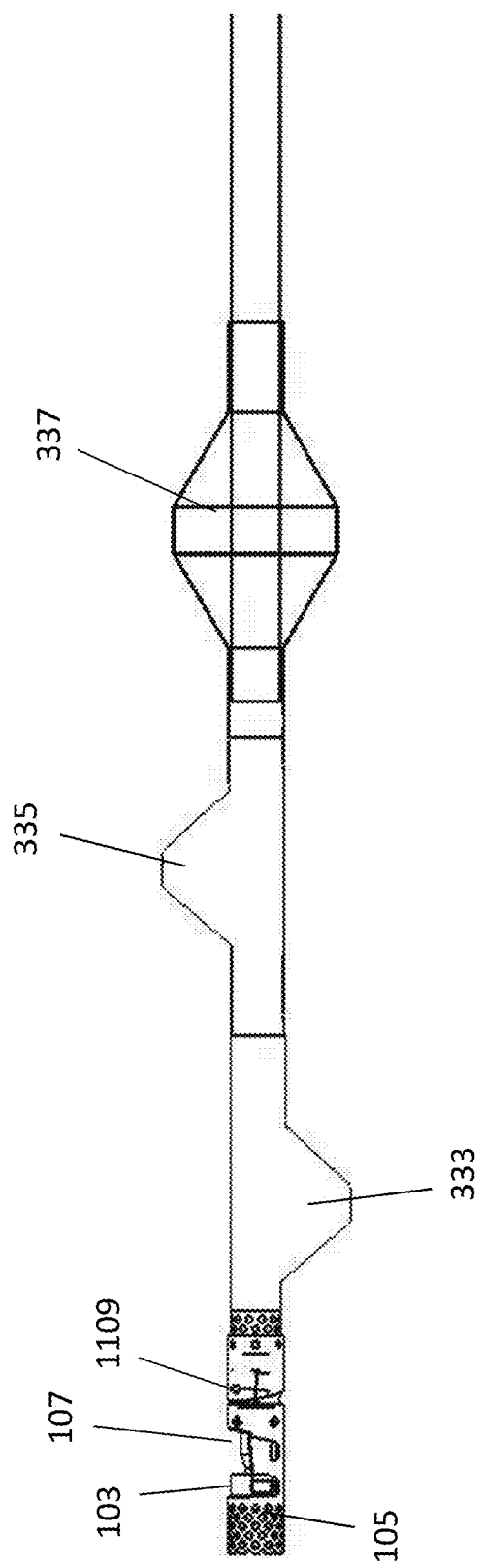
FIG. 6 shows one variation of a distal end of an atherectomy having a plurality of balloons that are arranged and may be used to provide a mechanical advantage in driving the cutting edge against the vessel wall.

Referring to FIG. 6, in some embodiments, the atherectomy catheters 100, 200, 400 can further include two or more balloons configured to help urge the cutter 103 into the tissue. The first balloon 333 can be the distal-most balloon. The first balloon 333 can be positioned proximate to the hinge point 1109 and opposite to the cutting window 1107. The balloon 333 can urge the cutter 103 against the tissue by deflecting the cutter 103 up and into the tissue. A second balloon 335, proximal to the distal balloon 333, can be on the same side of the catheter 100 as the cutting window 107 and can further help drive the cutter 103 into the tissue by. In some embodiments, the second balloon 335 can be annular. In some embodiments, the second balloon 335 can help occlude the vessel. Further, in some embodiments (and as shown in FIG. 6), a third balloon 337 can be used for occlusion. One or more of the balloons 333, 335, 337 can be configured to as to expand with little pressure, such as less than 2 psi. This low pressure advantageously prevents the balloons 333, 335, 337 from pushing hard against the vessel wall, but still provides enough pressure to urge the cutter 103 into the tissue. The balloons 333, 335, 337 can further include tapered edges on the proximal and distal edges that allow the balloon to slide along the vessel and/or fit through tortuous regions.

Figure 17A:
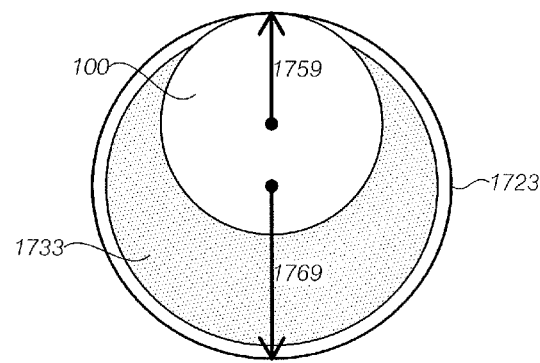
FIGS. 17A-17D show an atherectomy catheter with a crescent-shaped balloon.
Figure 17B:
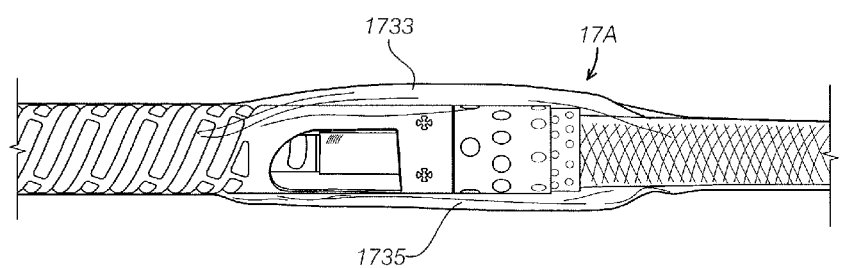
Figure 17C:
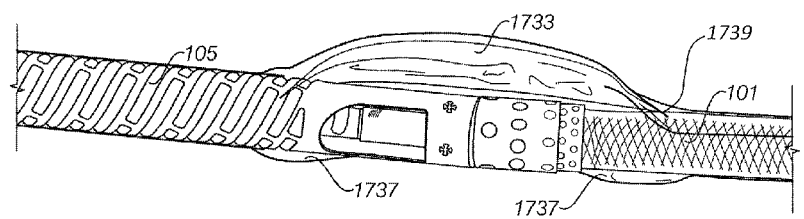
Figure 17D:
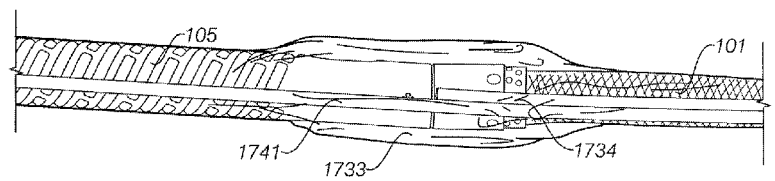

Referring to FIGS. 17A-17D, in another embodiment, the atherectomy catheters 100, 200, 400 can include a single balloon configured to both urge the cutter 103 into the tissue and occlude blood flow to improve imaging. Referring to FIG. 17A, the balloon 1733 can have a crescent shape, i.e., can be wrapped around the catheter 100 so as to cover the entire circumference of the catheter 100 except where the cutter 103 is exposed. By using a balloon 1733 with such a shape, the gaps between the catheter 100 and the vessel 1723 are substantially reduced, advantageously negating or reducing the localized flushing required to displace blood from the visual field. In one embodiment, to create the crescent shape, the balloon includes wide necks at both ends that are then wrapped around the nosecone 105 and elongate body 101 such that they cover at least half of the circumferential surface. FIG. 17B shows the wrapped balloon edges 1735 while FIG. 17C shows the wide necks 1737 fused at both ends. FIG. 17C shows an inflation port 1739 contained inside the balloon 1733 as well as a guidewire lumen 1741 that spans the length of the balloon 1733. In some embodiments, the balloon 1733 can be used to open or close the nosecone without requiring proximal or distal movement of the driveshaft.

Figure 5:
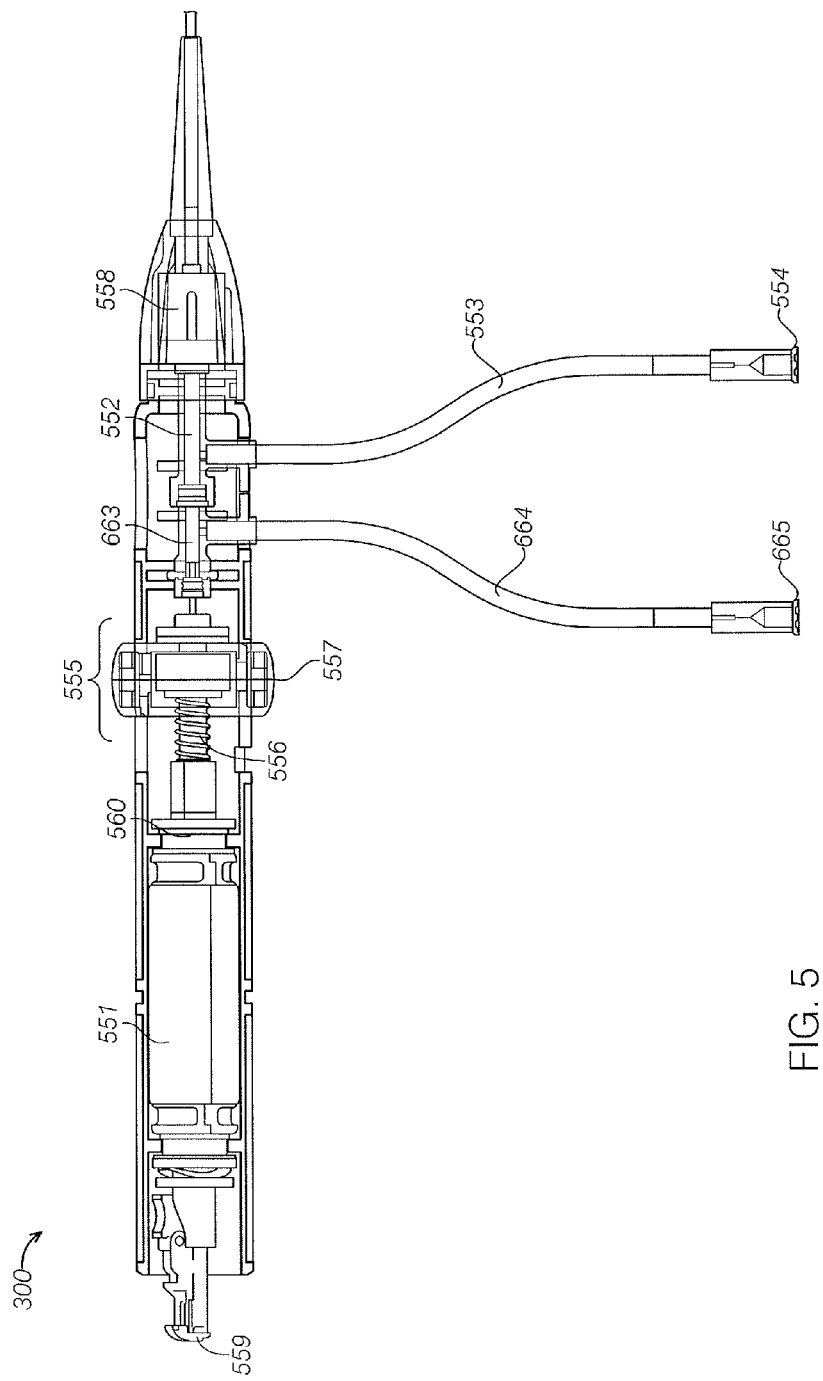
FIG. 5 illustrates a handle for an atherectomy catheter.

Referring to FIG. 5, a handle 300 can be used to control the rotation or translation of the driveshaft for the catheter 100, 200, or 400. The handle 300 can advantageously allow the optical fiber to move distally and proximally with the cutter as it is driven without requiring the fiber to move at a proximal location, e.g., without requiring movement of the optical fiber assembly within the drive assembly. Thus, the handle 300 can be design to completely account for movement of the drive shaft. An exemplary driveshaft management system 555 is shown in FIG. 5. The driveshaft management system 555 allows the user to position the driveshaft distally or proximally as the driveshaft is simultaneously spinning at a high speed. In some embodiments, the driveshaft can be configured such that it is fully tensioned before the driveshaft management system 555 is positioned at its most proximal position. That is, the driveshaft management system 555 can include a driveshaft tensioning spring 556. The spring 556 can be configured such that, as the user positions the slideable user ring 557 (or button) proximally, the driveshaft is fully tensioned and the driveshaft management system 555 is moved proximally, causing the spring 556 to compress and apply a controlled tensile load on the driveshaft. This fiber management system 555 advantageously enhances performance of the catheter by tensioning the driveshaft with a pre-determined load to properly position the cutting and imaging component against the bushing at the distal end of the catheter, improving cutting and imaging of the catheter.

The driveshaft management system 555 can transmit torque originating from a drive assembly, as described further below. Connection to the drive assembly can be made at the optical connector 559. Torque can thus be transmitted from the optical connector 559, through the fiber cradle 551, to the drive key 560, through the driveshaft management system 555, and then directly to the catheter driveshaft, all of which can rotate in conjunction. The fiber cradle 551 can include a set of components (i.e., a pair of pieces to make the whole fiber cradle) that houses the proximal end of the optical fiber and transmits torque within the driveshaft system. The fiber cradle components can be thin-walled by design, thereby creating a hollow space inside. Within this hollow space of the fiber cradle 551, the optical fiber can be inserted or withdrawn as the device driveshaft is positioned proximally or distally. As the fiber is inserted into the fiber cradle 551 when the user ring 557 is positioned proximally, the fiber is able to coil within the internal space of the fiber cradle 551 while maintaining imaging throughout its length to the distal tip. Conversely, as the fiber is withdrawn from the fiber cradle 551 when the user ring 557 is positioned distally, the coiled section of fiber is able to straighten while maintaining imaging throughout its length to the distal tip. This design feature advantageously provides more fiber capacity or "slack" to the overall driveshaft system to increase the range in which the driveshaft system can be translated.

The handle 300 can further include a balloon inflation chamber 552 configured to connect to a balloon inflation lumen (e.g., for use with a balloon on the catheter as described above) on one side and to balloon inflation tubing 553 and/or a port 554 on the other side. Because the inflation fluid transfers to the balloon through the balloon inflation chamber 552, the outer shaft 111 can advantageously rotate (e.g., by rotating the knob 558) independently of the balloon inflation chamber 552, allowing the tubing 553 and/or port 554 to remain stationary during rotation of the outer shaft 111.

Moreover, as shown in FIG. 5, the handle 300 can further include a catheter flush chamber 663 and catheter flush tubing 664 and/or flush port 665 to provide flushing through the catheter, as described above.

The catheters described herein can be driven using a drive assembly. Exemplary drive assemblies are described in co-pending patent applications: PCT Application No. PCT/US2013/032089, titled "ATHERECTOMY CATHETER DRIVE ASSEMBLIES," filed Mar. 15, 2013 (Publication No. WO 2013/172974), and U.S. patent application Ser. No. 13/654,357, titled "ATHERECTOMY CATHETERS AND NON-CONTACT ACTUATION MECHANISM FOR CATHETERS," filed Oct. 17, 2012 (Publication No. US-2013-0096589-A1), both of which are herein incorporated by reference in their entireties.

Figure 13A:
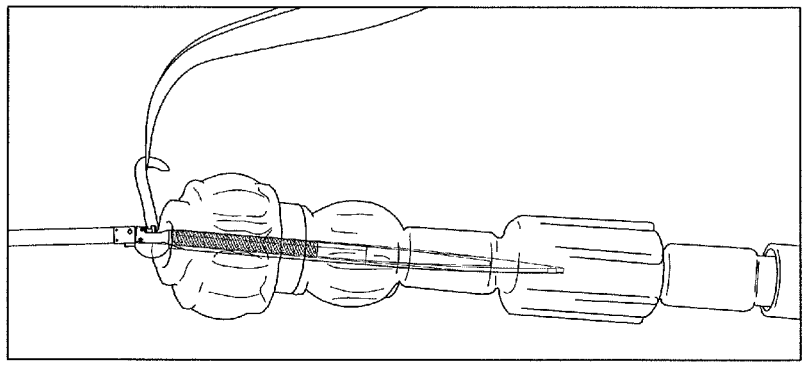
FIG. 13A shows the removal of a single, long strip of material cut from the tissue by an atherectomy catheter as described herein.
Figure 13B:
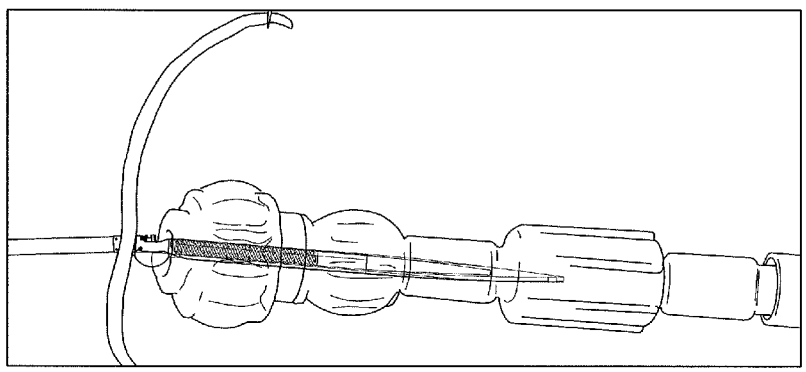
FIGS. 13B and 13C show the length of tissue removed.
Figure 13C:
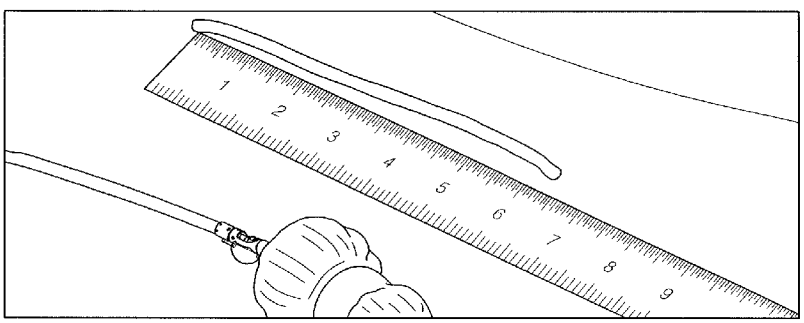

Advantageously, the atherectomy catheters 100, 200, 400 described herein can be used to remove strips of tissue. FIG. 13A shows the removal of a single, long strip of material cut from the tissue by an atherectomy catheter as described herein. FIGS. 13B and 13C show the length of tissue (weighting 70.4 mg) removed.

The atherectomy catheters described herein may additionally include any of the features described in the following co-pending applications: PCT Application No. PCT/US2013/031901, titled "ATHERECTOMY CATHERES WITH IMAGING," filed Mar. 15, 2013 (Publication No. WO 2013/172970), and PCT Application No. PCT/US2013/032494, titled "BALLOON ATHERECTOMY CATHERS WITH IMAGING," filed Mar. 15, 2013 (Publication No. WO 2014/039099), both of which are herein incorporated by reference herein in their entireties.

Occlusion-Crossing Catheters

Figure 14:
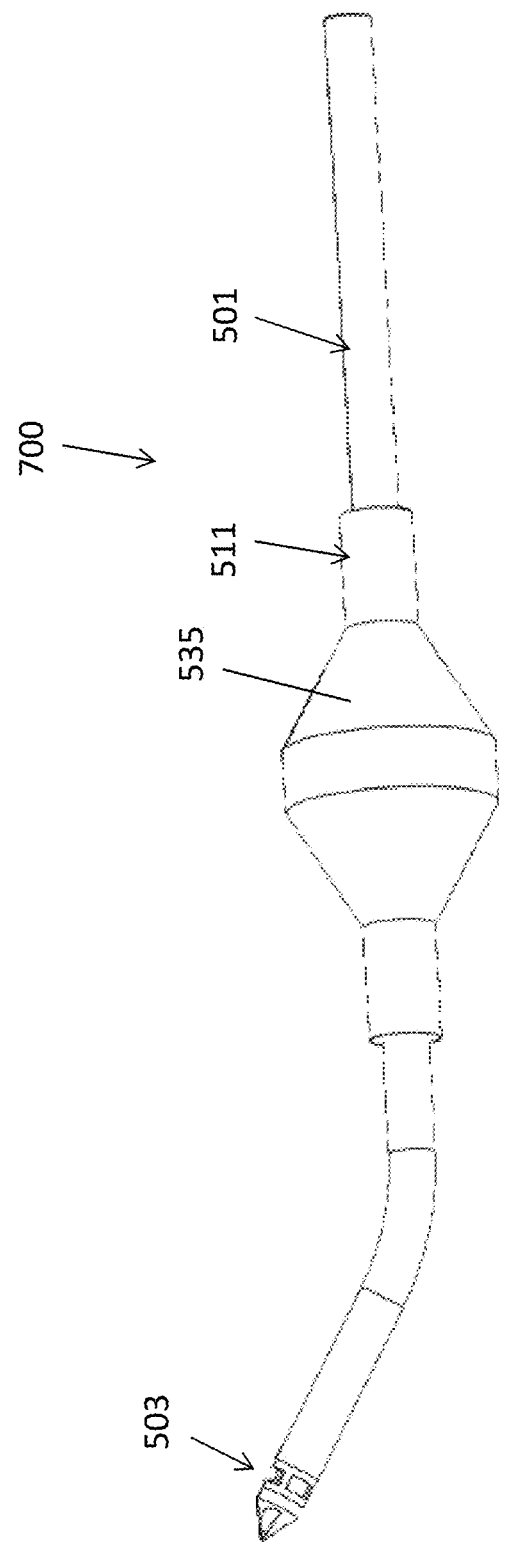
FIG. 14 shows an occlusion-crossing catheter.

Referring to FIG. 14, an occlusion-crossing catheter 700 can include an outer sheath 511 with a tapered occluding balloon 535 attached thereto.

In some embodiments, the cutting head 503 of the catheter 700 can be interchangeable, allowing the device to be more widely useable and adaptable. For example, the tip 503 can be interchangeable between a tip that is cone-shaped and burred (as shown by tip 503a in FIG. 15A), a tip that is fluted with cutting edges (as shown by tip 503b in FIG. 15B), a tip that is includes forward-projecting tips for aggressive cutting (as shown by tip 503c in FIG. 15C), and/or a tip that is chisel-like with a single sharp blade (as shown by tip 503d in FIG. 15D). In order to allow the tips to be interchangeable, the tips 503 can, for example, have a threaded proximal edge that threads in the opposite direction of rotation of the head 503. In other embodiments, the proximal edges can snap or otherwise fit in and out of the elongate body 501 of the device 700.

Additional Details

As noted above, the devices and techniques described herein can be used with OCT imaging. Exemplary imaging systems are described in co-pending applications: U.S. patent application Ser. No. 12/790,703, titled "OPTICAL COHERENCE TOMOGRAPHY FOR BIOLOGICAL IMAGING," filed May 28, 2010 (Publication No. US-2010-0305452-A1); U.S. patent application Ser. No. 12/829,267, titled "CATHETER-BASED OFF-AXIS OPTICAL COHERENCE TOMOGRAPHY IMAGING SYSTEM," filed Jul. 1, 2010 (now U.S. Pat. No. 9,125,562); International Patent Application No. PCT/US2013/031951, titled "OPTICAL COHERENCE TOMOGRAPHY WITH GRADED INDEX FIBER FOR BIOLOGICAL IMAGING," filed Mar. 15, 2013, Publication No. WO 2013/172972, all of which are herein incorporated by reference in their entireties.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An atherectomy catheter device having a multi-channeled bushing, the device comprising:
    an elongate body;
    a tip extending from a distal end of the elongate body;
    a drive shaft extending within the elongate body;
    a bushing comprising
        a bushing body,
        a hinge point on a side of the bushing body,
        a first channel extending proximally to distally through the bushing body,
        a second channel extending proximally to distally through the bushing body, overlapping with the first channel and having a diameter of the second channel that is less than a diameter of the first channel, and wherein the second channel is angled between 1° and 45° relative to the first channel,
        a first opening at a distal end of the bushing body into the first channel, and
        a second opening at the distal end of the bushing body into the second channel, wherein the first and second openings overlap; and
    a cutter having a distal cutting head with a cutting edge, an elongate cylindrical body, and a neck region extending between the distal cutting edge and the elongate cylindrical body, wherein the drive shaft is coupled to the elongate cylindrical body;
    further wherein distal movement of the drive shaft extends the cylindrical body of the cutter within the first channel of the bushing and drives the tip about the hinge point to axially align the tip with the elongate body and at least partially cover the cutting edge, while proximal movement of the drive shaft extends the neck region of the cutter within the second channel of the bushing and drives the tip about the hinge point to angle the tip relative to the elongate body and at least partially expose the cutting edge.

2. The device of claim 1, wherein the bushing comprises an inner flange positioned distal to the hinge, wherein distal movement of the drive shaft extends the cylindrical body of the cutter within the first channel of the bushing and drives the neck region against the inner flange portion to drive the tip about the hinge point to axially align the tip with the elongate body.

3. The device of claim 1, wherein the bushing comprises an outer flange at the distal end of the bushing, wherein proximal movement of the drive shaft extends the neck region of the cutter within the second channel of the bushing and drives the distal cutting head against the outer flange portion to drive the tip about the hinge point to angle the tip relative to the elongate body.

4. The device of claim 1, wherein the bushing comprises an outer flange at the distal end of the bushing, wherein proximal movement of the drive shaft extends the neck region of the cutter within the second channel of the bushing and drives the distal cutting head against the outer flange portion to drive the tip about the hinge point to angle the tip relative to the elongate body, further wherein the outer flange at the distal end of the bushing comprises a face that is angled relative to a central longitudinal axis of the elongate body.

5. The device of claim 1, wherein the second channel is angled between about 2° and 15° relative to the first channel.

6. The device of claim 1, wherein the hinge point is one of a pair of hinge points that are on either side of the bushing body and offset from a midline along a distal-to-proximal axis of the bushing body.

7. The device of claim 1, wherein the hinge point is part of a hinge channel formed through a top peripheral region of the bushing body, further wherein the hinge channel extends in a direction that is transverse to the first channel.

8. The device of claim 1, further comprising an optical fiber extending though the drive shaft and coupled to a reflector in the cutter to form an optical coherence tomography (OCT) imaging sensor.

9. The device of claim 1, wherein the cutter is configured to rotate within the bushing.

10. The device of claim 1, wherein the elongate cylindrical body of the cutter is configured to rotate within the bushing.

11. The device of claim 1, wherein the tip comprises a hollow tip.

12. The device of claim 1, wherein the cutter is configured to extend beyond the bushing and into the tip to pack tissue into the tip.

13. An atherectomy catheter device having a multi-channeled bushing, the device comprising:
    an elongate body;
    a tip extending from a distal end of the elongate body;
    a drive shaft extending within the elongate body;
    a bushing comprising
        a bushing body,
        a pair of hinge points on either side of the bushing body that are offset from a midline along a distal-to-proximal axis of the bushing body,
        an inner flange positioned distal to the hinge points
        a first channel extending proximally to distally through the bushing body,
        a second channel extending proximally to distally through the bushing body and having a diameter along a length of the second channel that is less than a diameter along a length of the first channel, and wherein the first and the second channels overlap, and wherein the second channel is angled between 1° and 45° relative to the first channel,
a first opening at a distal end of the bushing body into the first channel, and
a second opening at a distal end of the bushing body into the second channel, wherein the first and second openings overlap, and
an outer flange portion distal to the inner flange portion;
a cutter having a distal cutting head with a cutting edge, an elongate cylindrical body, and a neck region extending between the distal cutting edge and the elongate cylindrical body, wherein the drive shaft is coupled to the elongate cylindrical body; and
further wherein distal movement of the drive shaft extends the cylindrical body of the cutter within the first channel of the bushing, drives the neck region against the inner flange portion and drives the tip about the hinge points to axially align the tip with the elongate body at least partially covering the cutting edge, while proximal movement of the drive shaft extends the neck region of the cutter within the second channel of the bushing, drives the distal cutting head against the outer flange portion, and drives the tip about the hinge points to angle the tip relative to the elongate body and at least partially expose the cutting edge.

14. The device of claim 13, wherein the outer flange comprises a distal face at an angle of less than 90 degrees relative to a central longitudinal axis of the elongate body.

15. The device of claim 13, further comprising an optical fiber extending though the drive shaft and coupled to a reflector in the cutter to form an optical coherence tomography (OCT) imaging sensor.

16. The device of claim 13, wherein the cutter is configured to rotate within the bushing.

17. The device of claim 13, wherein the cutter is configured to extend beyond the bushing and into the tip to pack tissue into the tip.

18. The device of claim 13, wherein the second channel is angled between about 2° and 15° relative to the first channel.

19. The device of claim 13, wherein the hinge points form a channel through a top peripheral region of the bushing body, further wherein the hinge channel extends in a direction that is transverse to the first channel.

20. An atherectomy catheter device having a multi-channeled bushing, the device comprising:
an elongate body;
a hollow distal tip extending from a distal end of the elongate body;
a drive shaft extending within the elongate body;
a bushing comprising
a bushing body,
a pair of hinge points on either side of the bushing body that are offset from a midline along a distal-to-proximal axis of the bushing body,
an inner flange positioned distal to the hinge points
a first channel extending proximally to distally through the bushing body,
a second channel extending proximally to distally through the bushing body and having a diameter along a length of the second channel that is less than a diameter along a length of the first channel, and wherein the first and the second channels overlap, and wherein the second channel is angled between 1° and 45° relative to the first channel,
a first opening at a distal end of the bushing body into the first channel, and
a second opening at a distal end of the bushing body into the second channel, wherein the first and second openings overlap, and
an outer flange portion distal to the inner flange portion; and
a cutter having a distal cutting head with a cutting edge, an elongate cylindrical body, and a neck region extending between the distal cutting edge and the elongate cylindrical body, wherein the drive shaft is coupled to the elongate cylindrical body;
further wherein distal movement of the drive shaft extends the cylindrical body of the cutter within the first channel of the bushing and drives the hollow distal tip about the hinge points to axially align the hollow distal tip with the elongate body at least partially covering the cutting edge, while proximal movement of the drive shaft extends the neck region of the cutter within the second channel of the bushing and drives the hollow distal tip about the hinge points to angle the hollow distal tip relative to the elongate body and at least partially expose the cutting edge.

* * * * *